(12) United States Patent
Laurencin et al.

(10) Patent No.: US 8,927,018 B2
(45) Date of Patent: *Jan. 6, 2015

(54) IMMOBILIZED METALLIC NANOPARTICLES AS UNIQUE MATERIALS FOR THERAPEUTIC AND BIOSENSOR APPLICATIONS

(71) Applicant: University of Virginia Patent Foundation, Charlottesville, VA (US)

(72) Inventors: Cato T. Laurencin, Farmington, CT (US); Lakshmi Sreedharan Nair, Avon, CT (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/741,591

(22) Filed: Jan. 15, 2013

(65) Prior Publication Data
US 2013/0142885 A1 Jun. 6, 2013

Related U.S. Application Data

(62) Division of application No. 12/669,981, filed as application No. PCT/US2008/070875 on Jul. 23, 2008, now abandoned.

(60) Provisional application No. 60/961,587, filed on Jul. 23, 2007.

(51) Int. Cl.
| | | |
|---|---|---|
| *A61K 9/08* | (2006.01) |
| *A61K 31/722* | (2006.01) |
| *A61K 33/38* | (2006.01) |
| *A61L 27/04* | (2006.01) |
| *B82Y 30/00* | (2011.01) |
| *A61K 8/73* | (2006.01) |

(52) U.S. Cl.
CPC .................. *A61K 33/38* (2013.01); *A61K 8/736* (2013.01); *A61L 27/04* (2013.01); *A61L 2400/12* (2013.01); *B82Y 30/00* (2013.01)
USPC ........................................ 424/488; 424/78.17

(58) Field of Classification Search
None
See application file for complete search history.

(56) References Cited

U.S. PATENT DOCUMENTS

| | | | |
|---|---|---|---|
| 8,389,467 B2 * | 3/2013 | Chaput et al. | 514/1.1 |
| 2007/0160647 A1 * | 7/2007 | Pritchard et al. | 424/423 |
| 2009/0149421 A1 * | 6/2009 | Buschmann et al. | 514/55 |

OTHER PUBLICATIONS

Nair, et al., Development of Injectable Thermogelling Chitosan—Inorganic Phosphate Solutions for Biomedical Applications, Biomacromolecules 2007, 8, 3779-3785.*

* cited by examiner

*Primary Examiner* — H. Sarah Park
(74) *Attorney, Agent, or Firm* — Rodney L. Sparks

(57) ABSTRACT

The present invention relates to compositions and methods by which surface modification techniques can be used to modify wide range polymeric or metal substrates using metal nanoparticles.

11 Claims, 23 Drawing Sheets

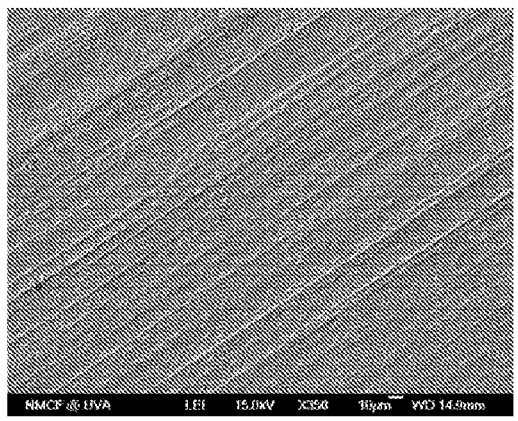 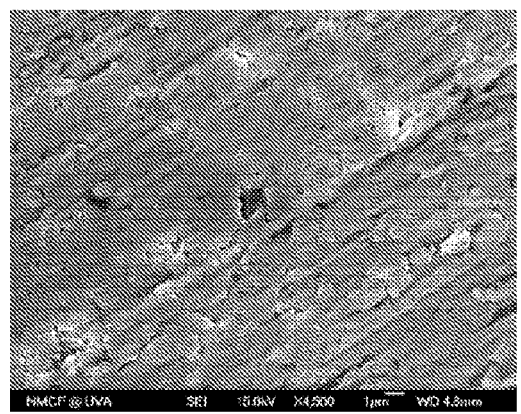
FIG. 1A FIG. 1B
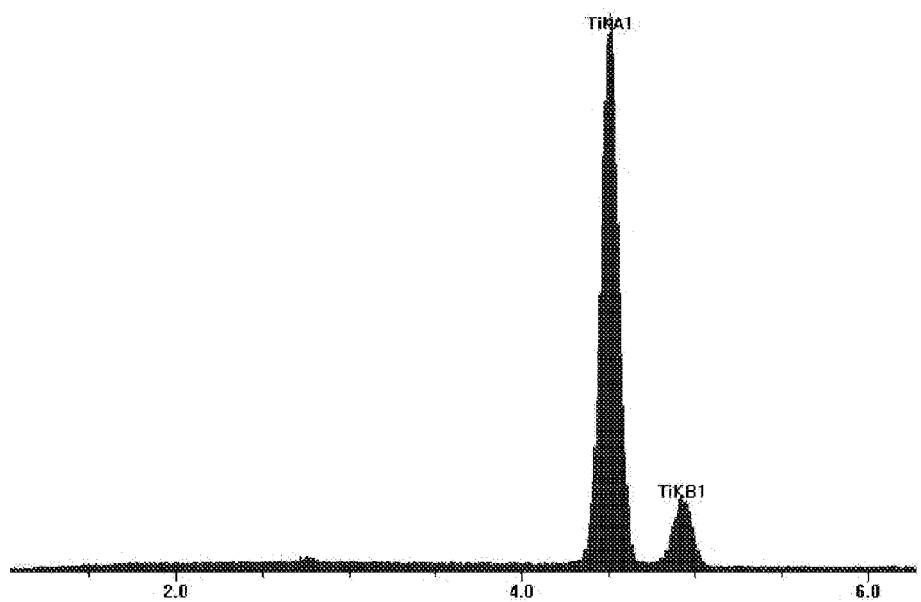
FIG. 2

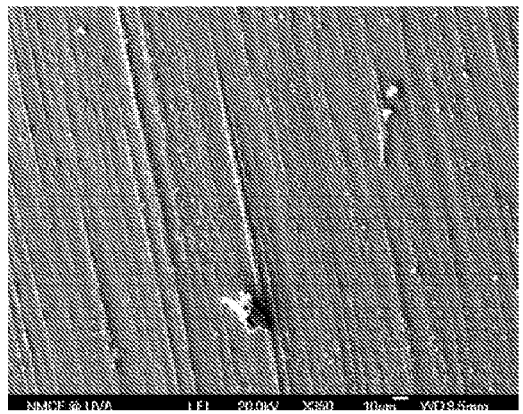
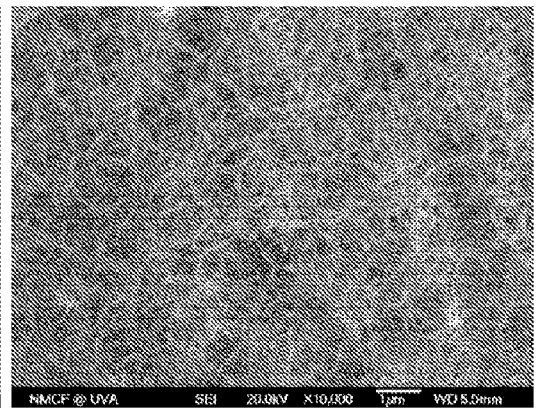
FIG. 9A         FIG. 9B
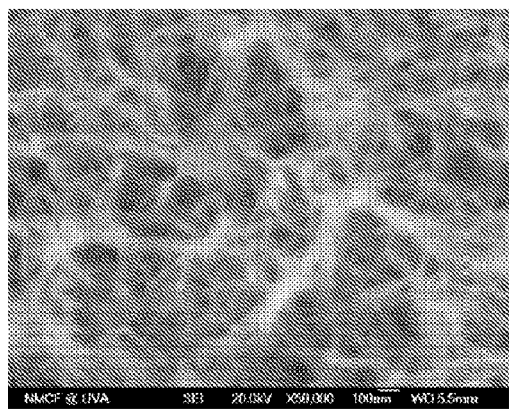
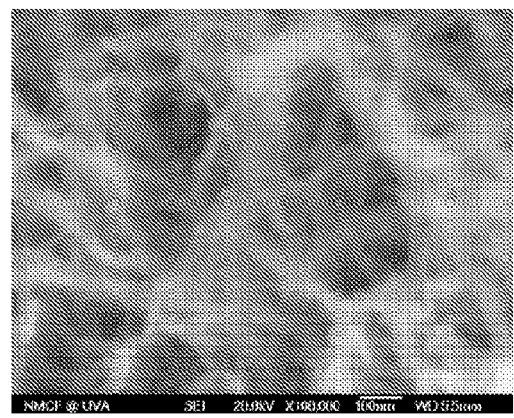
FIG. 9C         FIG. 9D
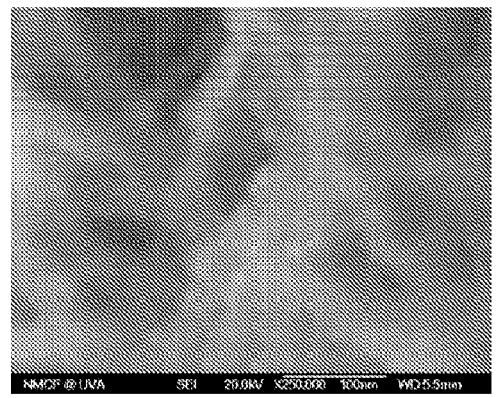
FIG. 9E

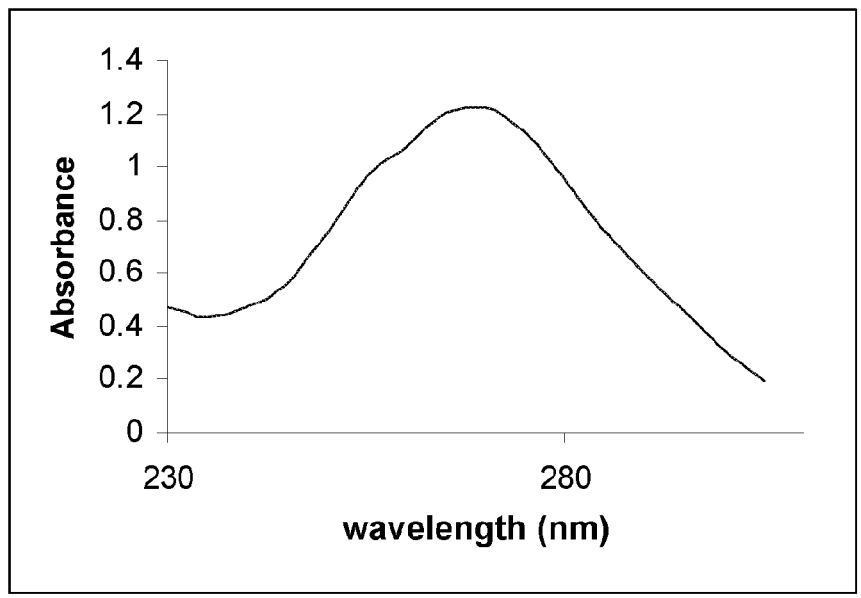
FIG. 12
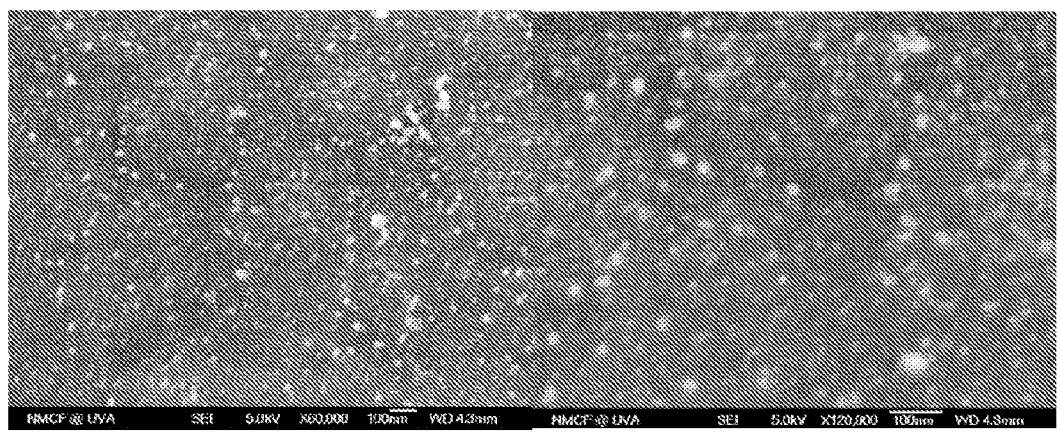
FIG. 13A          FIG. 13B

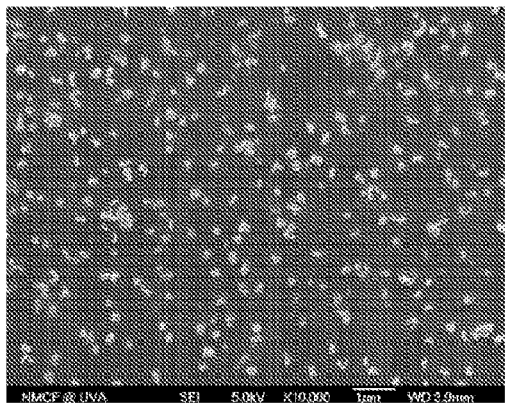 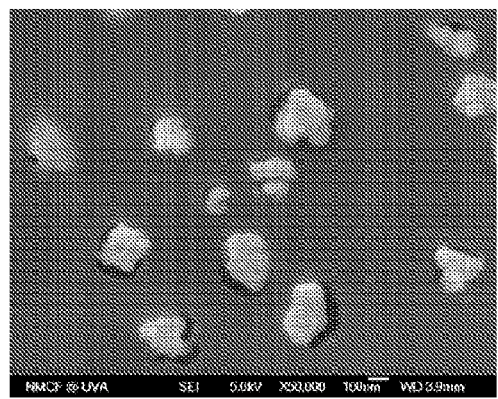
FIG. 15A  FIG. 15B
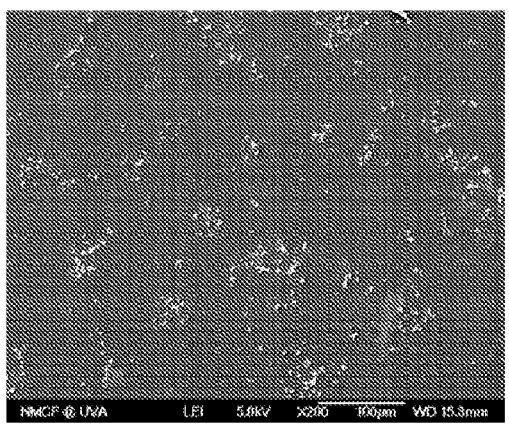 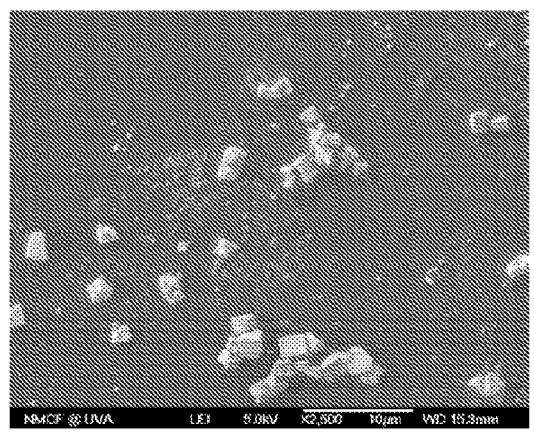
FIG. 16A  FIG. 16B
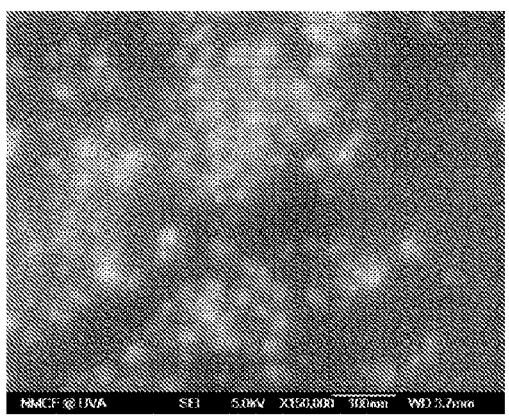 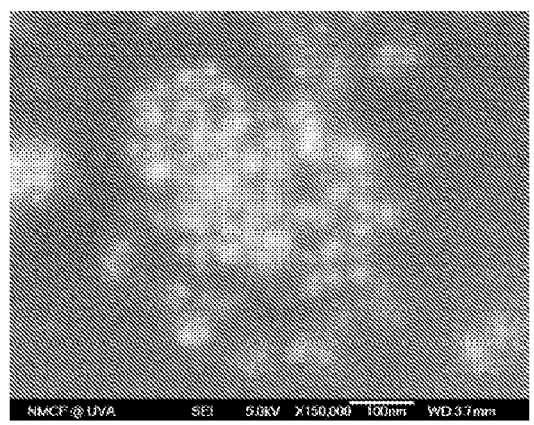
FIG. 16C  FIG. 16D

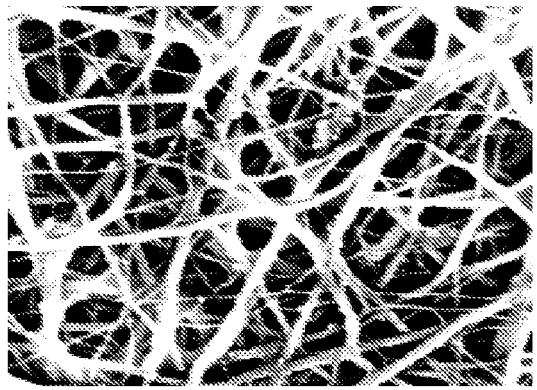
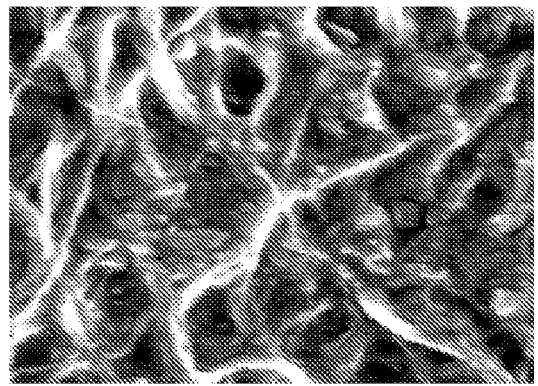
FIG. 18A   FIG. 18B
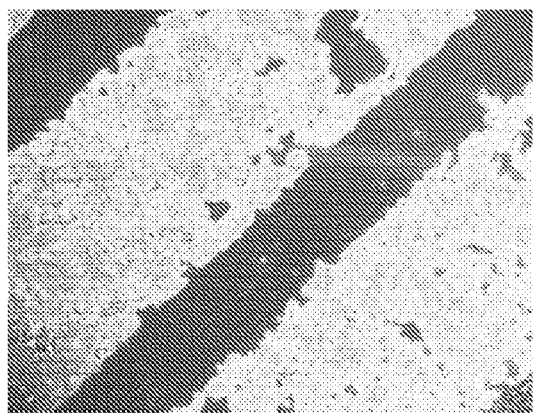
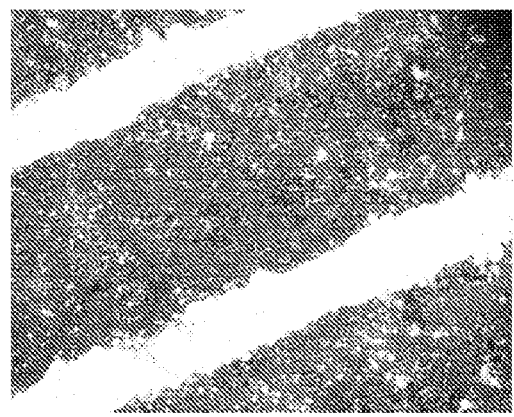
FIG. 19A   FIG. 19B

IMMOBILIZED METALLIC NANOPARTICLES AS UNIQUE MATERIALS FOR THERAPEUTIC AND BIOSENSOR APPLICATIONS

CROSS REFERENCE TO RELATED APPLICATIONS

This application is a divisional of U.S. application Ser. No. 12/669,981, filed Jan. 21, 2010, which is a national stage filing of International Application No. PCT/US2008/070875, filed Jul. 23, 2008, which is entitled to priority pursuant to 35 U.S.C. §119(e) to U.S. provisional patent application No. 60/961,587, filed on Jul. 23, 2007. The entire disclosures of the afore-mentioned patent applications are incorporated herein by reference.

FIELD OF INVENTION

This invention relates generally to methods and compositions useful for adding metallic nanoparticles to various substrates.

BACKGROUND

Nanoparticles have been broadly defined as particles having one or more dimensions of the order of 100 nm or less. Even though various materials such as polymers, ceramics, metals and organic molecules are being currently investigated for developing nanosized particles, metal nanoparticles have raised significant interest due to their unique properties.

Nanosized metallic particles, mainly gold and silver nanoparticles, have attracted attention because of their unique optical and electrical properties, as well as potential biomedical applications. Thus, depending upon their size, shape, surface area, surface plasmon and surface chemistry, these metallic nanoparticles are known to show distinct optical, magnetic, electrical and biological properties which are different from the bulk materials [1].

Due to their unique properties and various areas of applications such as infection resistance, catalysis, nanoelectronics, optical filters and surface raman scattering, nanoparticles of silver are one of the most extensively investigated metallic nanoparticles [2]. Several techniques have already been developed to form metal nanoparticles in solution. Thus, silver nanoparticles are commonly prepared by the controlled reduction of silver salt solutions. The structure and corresponding physical, chemical, and biological properties of silver nanoparticles are known to strongly depend on the method of preparation and the experimental conditions [3]. Several reduction techniques have been investigated. These reduction techniques include strong chemical reducing agents such as sodium borohydride and hydrazine, irradiation using gamma rays, ultra violet, and visible light, microwave as well as ultra sound, and weak reducing agents such as ascorbates, citrates, alcohol, as well as polyols.

Even though colloidal solutions of silver exhibit unique optical and biological properties, the assembly of these particles into thin films is highly recommended for the development of practical applications [4]. Recently, techniques have been developed to immobilize silver nanoparticles on surfaces via surface modification techniques [5].

Various preparation routes for composite materials have been proposed.

These include self assembly [6], electroless plating [7], layer by layer (LBL) self assembly of polyelectrolytes and metal nanoparticles [8] and ultra sound irradiation [9]. Most of these approaches tend to produce surfaces coated with metal nanoparticles by physical adsorption or electrostatic interactions and are not highly suitable for practical biomedical applications. Recently, physical vapor deposition or magnetron sputtering has been investigated to develop thin nanostructured silver surfaces for a variety of applications. A radiofrequency magnetron source is commonly used for the sputtering process to deposit porous nanocrystalline metallic silver on surfaces.

A surface produced by magnetron sputtering of silver has been shown to have strong antibacterial properties [10]. The antibacterial property has been attributed to the release of silver ions from the surface in a controlled and appropriate concentration. In addition to antibacterial properties, the modified surface has wound healing properties, demonstrating the advantages of silver coated materials for biomedical applications [11]. Even though it is highly effective, the fabrication process has several limitations to be used for practical applications. These include the lack of flexibility and controllability of the process, the limited range of materials that can be modified and the limited surface area that can be modified at a time.

There is a long felt need in the art for compositions and methods by which surface modification techniques can be used to modify wide range polymeric substrates using metal nanoparticles as well as for metallic substrates. The present invention satisfies these needs.

SUMMARY OF THE INVENTION

The present disclosure demonstrates the development of mild and cost effective methods to immobilize metallic nanoparticles on polymeric or metallic substrates. This involves unique and mild processes to immobilize soft templates on the surface of polymeric materials which can be used to fabricate silver or gold nanoparticles by ion exchange method. The immobilization on polymeric substrates involves coating the surface with a photoactive polymer capable of synthesizing metallic nanoparticle on the surface. In one aspect, the template can be immobilized on any polymeric substrate using a mild and fast (1-2 minutes) photoreaction. The process is highly versatile as it can be used to create metallic nanoparticles such as silver nanoparticles on a wide range of polymeric substrates irrespective of its physical form, shape, or chemistry. A related method has also been designed for metallic biomaterials such as titanium. The data disclosed herein demonstrate the feasibility of synthesizing silver nanoparticles of different size ranges on the substrate surface depending on the reaction conditions. Furthermore, the process allows the feasibility of patterning surfaces with metallic nanoparticles demonstrating its potential for biosensor applications.

In one aspect, the procedure is based on the photochemistry of azide groups which has been extensively investigated previously for lithographic techniques [12]. The present invention utilizes, inter alia, azide chemistry to immobilize a wide range of natural and synthetic polymers on biomaterial surfaces and use the immobilized polymers as templates to synthesis metallic nanoparticles.

In one aspect, the present invention encompasses practical methods to immobilize metal nanoparticles on any polymeric substrates. In another aspect, the present invention encompasses a nondestructive modification process without the use of harsh chemicals or high energy radiation. In another aspect, the present invention encompasses modifying polymeric substrates having any shape or size or structure. In yet another aspect, the present invention encompasses a practical method to immobilize nanoparticles on a metal surface. In one aspect, the metal surface comprises titanium.

In a further aspect, the present invention encompasses compositions and methods useful for controlling the size and distribution of nanoparticles on the surface by varying parameters associated with the template as well as other reagents. The present invention also encompasses compositions and methods useful for developing a green process without the use of reducing agents.

In one aspect, the surface is metal. In one aspect, the metal is titanium. In one aspect, the metal surface is etched. In one aspect, the metal surface comprises metal nanoparticles. In one aspect, the metal nanoparticles are silver nanoparticles. In one aspect, the silver particles are about, 0.1 to about 100 nm in size or from about 1 to about 100 nm in size. In another aspect, they are 2-75 nm in size. In yet another aspect, they are about 3-50 nm in size. In a further aspect, they are about 4-25 nm. In another aspect, they are about 5-10 nm in size.

In one aspect, the metal substrates and metal films of the invention are useful as surfaces for culturing mammalian cells. By the term "culturing" mammalian cells or "maintaining cells in culture" is meant that the cells will adhere to the surface, but does not exclude the possibility that the cells merely adhere and do not proliferate. In one aspect, the metal substrates and metal films of the invention support the proliferation and differentiation of cells selected from the group consisting of stem cells, pluripotent stem cells, committed stem cells, embryonic stem cells, adult stem cells, bone marrow stem cells, bone marrow-derived stem cells, adipose stem cells, umbilical cord stem cells, dura mater stem cells, precursor cells, differentiated cells, osteoblasts, osteoclasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, normal cells, cancer cells, Schwann cells, and neurons. In one aspect, the cells are human cells. In one aspect, metal substrates and films of the invention comprising cells can be used as delivery vehicles to deliver the cells to a site of interest in a subject in need thereof.

Other materials may also be added to the metal films and substrates, in addition to metal nanoparticles such as silver nanoparticles.

In one aspect, the metal substrates and films of the invention are useful for inhibiting microbial growth. In one aspect, the microbial growth is bacterial growth.

In one embodiment, the metal substrates are useful as nanostructured implants. In one aspect, the nanostructured implants can increase osseointegration and provide matrices to be used to deliver cells such as hMSCs to an osseous defect and reduce implant associated infection. Therefore, the present invention encompasses the use of metal substrates, particularly those which are etched or comprise metallic nanoparticles, as delivery vehicles. These delivery vehicles can be used to deliver cells and other materials to a site in a subject in need thereof, including, but not limited to, a wound, an osseous defect, etc. The additional materials include, but are not limited, other cell types, additional therapeutic agents, hormones, growth factors, etc. The present application further discloses a versatile technique to develop nanostructured titanium containing silver nanoparticles as a potential biomaterial.

In one embodiment, the present application discloses a method of making polymeric substrates comprising metallic nanoparticles. This method comprises forming a photoactive polymer by contacting a polymer comprising a reactive group with an aromatic azide or aliphatic azide. It further comprises contacting the photoactive polymer with the polymeric substrate, and immobilizing the photoactive polymer to the polymeric substrate by irradiation. The method further encompasses contacting the polymeric substrate comprising immobilized photoactivated polymers with a composition comprising a metal for forming metallic nanoparticles and optionally washing the substrate after the contact. In one aspect, the polymeric substrate is polystyrene. In one aspect, the polymer comprising a reactive group is selected from the group consisting of poly(acrylic acid), alginica acid, heparin, and chondroitin sulfate. In one aspect, the azidated polymer is purified following azidation. In one aspect, the purified azidated polymer is dried. In one aspect, before contacting the polymeric substrate the dried purified azidated polymer is resuspended at concentrations selected from the group consisting of 10 mg/ml, 5.0 mg/ml, 1.0 mg/ml, and 0.05 mg/ml. In one aspect, the irradiation is ultraviolet irradiation. In one aspect, the wavelength of the ultraviolet irradiation is about 275 nm. In one aspect, the composition comprises silver. In one aspect, the immobilized silver is reduced from silver ion to silver metal. In one aspect, the silver nanoparticles are made using ammoniacal polysaccharides.

In one embodiment, the polymers are applied in patterns.

The present invention further encompasses a polymeric substrate comprising metallic nanoparticles made by the method described herein.

In one aspect, the metallic nanoparticles range in size from about 1.0 nm to about 100 nm. In another aspect, the nanoparticles range in size from about 2.0 nm to about 75 nm. In a further aspect, the nanoparticles range in size from about 3.0 nm to about 50 nm. In yet another aspect, the nanoparticles range in size from about 4.0 nm to about 25 nm. In another aspect, the nanoparticles range in size from about 5.0 nm to about 10.0 nm.

In one aspect, silver particles are incorporated onto the surface.

The present application encompasses the use of surface active copolymers. In one aspect, the surface active copolymers, include, but are not limited to, poloxamers, meroxapols, and poloxamines.

Examples of poloxamers include poloxamer-101, -105, -105 benzoate, -108, -122, -123, -124, -181, -182, -182 dibenzoate, -183, -184, -185, -188, -212, -215, -217, -231, -234, -235, -237, -238, -282, -284, -288, -331, -333, -334, -335, -338, -401, -402, -403, and -407. In one aspect, the poloxamer is poloxamer-188. In another aspect, the poloxamer is poloxamer-407.

In one embodiment, the surface active copolymer composition comprises PluroGel™ (PluroGen, Annapolis, Md.).

Exemplary meroxapols include, but are not limited to, meroxapol 105, 108, 171, 172, 174, 178, 251, 252, 254, 258, 311, 312, and 314.

Exemplary poloxamines include, but are not limited to, poloxamine 304, 504, 701, 702, 704, 707, 901, 904, 908, 1101, 1102, 1104, 1301, 1302, 1304, 1307, 1501, 1502, 1504, and 1508.

The present invention further encompasses methods for making metallic nanoparticles in chitosan and carboxymethyl chitosan. In one aspect, chitosan or carboxymethyl chitosan solutions are prepared in layers, which after drying, are contacted with a composition comprising a metal, which metal permeates the layers and forms metallic nanoparticles. In one aspect, the layers are alternated between chitosan and carboxymethyl chitosan. In one aspect, the metal is silver. One of ordinary skill in the art will appreciate that the conditions may be varied to adjust the size of nanoparticles formed, the number of nanoparticles formed, etc.

The present application further discloses a method of making a tri-layer membrane comprising metallic nanoparticles for use as a therapeutic agent or a biosensor. The method encompasses preparing a chitosan solution and preparing a carboxymethyl chitosan solution. Then, a first layer of solution is applied to a surface and allowed to dry. The method further encompasses applying a second layer comprising the other solution to the dried first layer and allowing the second layer to dry. The method also encompasses applying a third layer of the same solution as applied for the first layer over the second layer and allowing the third layer to dry. Optionally dried layers are heated. The dried layers are then neutralized. The neutralized layers are then contacted with a composition comprising a metal for forming metallic nanoparticles to form a tri-layer membrane comprising metallic nanoparticles.

One of ordinary skill in the art will appreciate that the methods and compositions of the invention can be varied or adjusted as needed to utilized different metals, form different numbers of nanoparticles, different sizes of nanoparticles, add additional agents, etc. For example, one of ordinary skill in the art will appreciate that reaction times, temperatures, concentrations of solutions, etc. can be varied.

In one aspect, the metallic particles are about, 0.1 to about 100 nm in size or from about 1 to about 100 nm in size. In another aspect, they are 2-75 nm in size. In yet another aspect, they are about 3-50 nm in size. In a further aspect, they are about 4-25 nm. In another aspect, they are about 5-10 nm in size.

Metals encompassed by the invention include gold (Au), silver (Ag), platinum (Pt), aluminum (Al), nickel (Ni), iron (Fe), palladium (Pd), titanium (Ti), scandium (Sc), vanadium (V), chromium (Cr), magnesium (Mg), manganese (Mn), cobalt (Co), copper (Cu), zinc (Zn), yttrium (Y), zirconium (Zr), niobium (Nb), molybdenum (Mo), technetium (Tc), ruthenium (Ru), cadmium (Cd), lutetium (Lu), hafnium (Hf), tungsten (W), rhenium (Re), osmium (Os), iridium (Ir), tantalum (Ta), rhodium (Rh), rare-earth metals ytterbium (Yb), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutecium (Lu). In one aspect, the metals are useful for making nanoparticles. In another aspect, the metals are useful in surfaces for immobilization of nanoparticles.

Various aspects and embodiments of the invention are described in further detail below.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1. Surface morphology of titanium thin films illustrated by scanning electron microscopic images at two different magnifications (1A—lower magnification (×350); 1B—higher magnification (×4,500); lower portion of image has magnification and bars indicating relative length).

FIG. 2. Surface elemental composition of titanium indicating the presence of only titanium atoms.

FIG. 7, comprising

FIG. 9, comprising FIGS. 9A-E, depicts surface morphologies of sodium borohydrode reduced titanium metal surface at various magnifications (×350, 10,000, 50,000, 100,000, and 250,000, respectively).

FIGS. 11A-11D, represents photographic images of: A. titanium metal surface; B. Titanium surface alkali etched; C. Titanium surface after treating with silver salt solution; D. Titanium surface after reduction to silver nanoparticles.

FIG. 12 graphically represents a UV spectrum of azidated alginic acid showing the presence of azide groups. The ordinate represents absorbance and the abscissa represent wavelength (nm)

FIG. 13. Silver nanoparticles formed on polystyrene substrates coated with polyacrylic acid, silver ion exchange and subsequent reduction (two magnifications indicating particles with size less than 50 nm; 13A—×60,000; 13B—×120,000).

FIG. 14, comprising

FIG. 15. Silver particles formed on azidated poly(acrylic acid) where in silver ions were exchanged for 5 h followed by reduction using sodium borohydride. Comparatively larger particles were obtained in this process. 15A indicates a lower magnification and 15B, a higher magnification during scanning electron microscopy.

FIG. 16, comprising FIGS. 16A-16D, depicts photographic images illustrating the formation of silver nanoparticles on azidated heparin sulfate coated on polystyrene substrate, after silver ion exchange and reduction using sodium borohydride.

FIG. 18. SEM showing the formation of silver nanoparticles on nanofiber matrices after a thin layer of coating with azidated polymers. A. Coating with dilute solution; B. Coating with concentrated solution.

FIG. 19, comprising FIGS. 19A and 19B, shows poly (acrylic azide) coated and shined with UV light through a photomask (19A). The lighter colored region (appears yellow in a color photograph) shows polyacrylic acid grafted on polystyrene surface. FIG. 19B shows silver nanoparticles formed on the polyacrylic acid patterns on polystyrene.

(FIG. 22A), PluroGel plus silver particles at 4° C. (22B), and PluroGel plus silver particles at 37° C. (22C). The phase transition is also apparent (note that the vial labeled C is upside down and the composition had gelled).

FIG. 26, comprising FIG. 26B represents a higher magnification image of silver nanoparticles and demonstrates the partially crystalline structure. FIG. 26C represents an x-ray diffraction pattern which confirms the partially crystalline structure of the particles.

FIG. 27, comprising FIGS. 27A-27D, graphically illustrates LTV absorption spectra collected at various times up to 24 hours and demonstrates the growth of silver particles as a function of time of incubation in silver nitrate solution. Data were obtained using a UV-Vis spectrophotometer and indicate the plasmon resonance of silver particles. FIGS. 27A—1 hour; 27B—3 hours; 27C—5 hours; and 27D—24 hours. It can be seen that by 3 hours (FIG. 27B), a characteristic peak of silver nanoparticles is present at 410-450 nm, and that by 24 hours (FIG. 27D) there is a significant increase in the peak. The abscissa represents wavelength in nanometers (nm). The ordinate represents optical density (OD).

FIG. 32, comprising FIG. 32A depicts an image of a scanning electron micrograph showing human bone marrow-derived mesenchymal stem cells on base-etched titanium film after 14 days in culture. FIG. 32B depicts a film modified with silver nanoparticles (arrow indicating silver nanoparticles).

DETAILED DESCRIPTION OF THE INVENTION

Figure 3A:
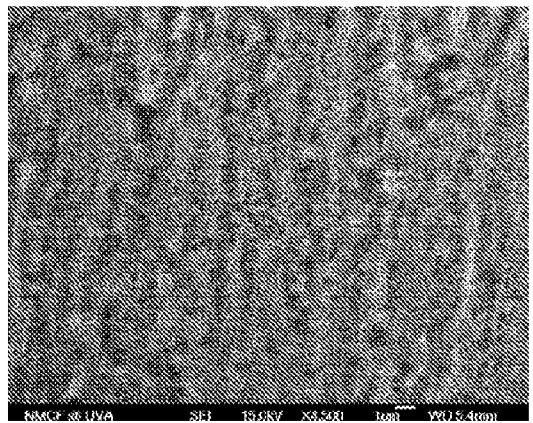
FIG. 3. Surface morphology of etched titanium thin films illustrated by scanning electron microscopic images at two different magnifications (3A—×4,500; 3B—×15,000).

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section. Specific and preferred values listed below for radicals, substituents, and ranges are for illustration only; they do not exclude other defined values or other values within defined ranges for the radicals and substituents.

DEFINITIONS

As used herein, the singular forms "a," "an," and "the" include plural reference unless the context clearly dictates otherwise.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated. Disease and disorders being treated by the additional therapeutically active agent include, for example, hypertension and diabetes. The additional compounds may also be used to treat symptoms associated with the injury, disease or disorder, including, but not limited to, pain and inflammation. Such compounds or agents include, but are not limited to drugs, antimicrobials, growth factors, cytokines, etc.

A disease, condition, or disorder is "alleviated" if the severity of a symptom of the disease, condition, or disorder, or the frequency with which such a symptom is experienced by a subject, or both, are reduced.

As used herein, an "analog" of a chemical compound is a compound that, by way of example, resembles another in structure but is not necessarily an isomer (e.g., 5-fluorouracil is an analog of thymine).

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

"Antiviral agent," as used herein means a composition of matter which, when delivered to a cell, is capable of preventing replication of a virus in the cell, preventing infection of the cell by a virus, or reversing a physiological effect of infection of the cell by a virus. Antiviral agents are well known and described in the literature. By way of example, AZT (zidovudine, Retrovir® Glaxo Wellcome Inc., Research Triangle Park, N.C.) is an antiviral agent which is thought to prevent replication of HIV in human cells.

The term "biocompatible," as used herein, refers to a material that does not elicit a substantial detrimental response in the host.

The term "biodegradable," as used herein, means capable of being biologically decomposed. A biodegradable material differs from a non-biodegradable material in that a biodegradable material can be biologically decomposed into units which may be either removed from the biological system and/or chemically incorporated into the biological system.

The term "bioresorbable," as used herein, refers to the ability of a material to be resorbed in vivo. "Full" resorption means that no significant extracellular fragments remain. The resorption process involves elimination of the original implant materials through the action of body fluids, enzymes, or cells. Resorbed calcium carbonate may, for example, be redeposited as bone mineral, or by being otherwise re-utilized within the body, or excreted. "Strongly bioresorbable," as the term is used herein, means that at least 80% of the total mass of material implanted is resorbed within one year.

As used herein "burn" or "burns" refer to any detectable injury to tissue caused by energy applied to the tissue. The terms "burn" or "burns" further refer to any burning, or charring of the tissue, including thermal burns caused by contact with flames, hot liquids, hot surfaces, and other sources of high heat as well as steam, chemical burns, radiation, and electrical burns. First degree burns show redness; second degree burns show vesication; third degree burns show necrosis through the entire skin. Burns of the first and second degree are partial-thickness burns, those of the third degree are full-thickness burns.

The term "clearance," as used herein refers to the physiological process of removing a compound or molecule, such as by diffusion, exfoliation, removal via the bloodstream, and excretion in urine, or via sweat or other fluid.

A "compound," as used herein, refers to any type of substance or agent that is commonly considered a drug, or a candidate for use as a drug, as well as combinations and mixtures of the above.

A "control" subject is a subject having the same characteristics as a test subject, such as a similar type of dependence, etc. The control subject may, for example, be examined at precisely or nearly the same time the test subject is being treated or examined. The control subject may also, for example, be examined at a time distant from the time at which the test subject is examined, and the results of the examination of the control subject may be recorded so that the recorded results may be compared with results obtained by examination of a test subject.

A "test" subject is a subject being treated.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

The term "decreased blood flow", as used herein, refers to a decrease in blood flow at a site of injury, disease, or disorder, and includes, but is not limited, a decrease in flow rate, an increase in stasis, and an increase in sludging in the vessels.

The term "delivery vehicle" refers to any kind of device or material which can be used to deliver cells in vivo or can be added to a composition comprising cells administered to an animal. This includes, but is not limited to, implantable devices, matrix materials, gels, etc.

As used herein, a "derivative" of a compound refers to a chemical compound that may be produced from another compound of similar structure in one or more steps, as in replacement of H by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, but are not limited to, radioactive isotopes, antigenic determinants, enzymes, nucleic acids available for hybridization, chromophores, fluorophores, chemiluminescent molecules, electrochemically detectable molecules, and molecules that provide for altered fluorescence polarization or altered light scattering.

A "disease" is a state of health of an animal wherein the animal cannot maintain homeostasis, and wherein if the disease is not ameliorated then the animal's health continues to deteriorate. As used herein, normal aging is included as a disease.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

The term "enhancing bone repair" as used herein refers to methods of speeding up or inducing better bone repair using compounds of the invention, relative to the speed or amount of bone repair that occurs without administration of compounds of the invention.

As used herein, a "functional" molecule is a molecule in a form in which it exhibits a property or activity by which it is characterized. A functional enzyme, for example, is one that exhibits the characteristic catalytic activity by which the enzyme is characterized.

"Graft" refers to any free (unattached) cell, tissue, or organ for transplantation.

"Allograft" refers to a transplanted cell, tissue, or organ derived from a different animal of the same species.

"Xenograft" refers to a transplanted cell, tissue, or organ derived from an animal of a different species.

The term "growth factor" as used herein means a bioactive molecule that promotes the proliferation of a cell or tissue. Growth factors useful in the present invention include, but are not limited to, transforming growth factor-alpha (TGF-α), transforming growth factor-beta (TGF-β), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5 s, NGF 7.0 s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, BY8, VEGF-E, granulocyte colony stimulating factor (G-CSF), insulin like growth factor (IGF) I and II, hepatocyte growth factor, glial neurotrophic growth factor, stem cell factor (SCF), keratinocyte growth factor (KGF), skeletal growth factor, bone matrix derived growth factors, and bone derived growth factors and mixtures thereof. Some growth factors may also promote differentiation of a cell or tissue. TGF, for example, may promote growth and/or differentiation of a cell or tissue.

The term "improved blood flow," as used herein, refers to increased blood flow in a subject being treated according to the methods of the invention compared with the flow in a subject with an otherwise identical injury or condition not being treated according to the methods of the invention. Improved flow is determined by methods such as those described herein and can include less stasis, less sludging, or a combination of both, in the subject being treated compared with the untreated subject.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, "injury" generally refers to damage, harm, or hurt; usually applied to damage inflicted on the body by an external force.

As used herein, an "instructional material" includes a publication, a recording, a diagram, or any other medium of expression which can be used to communicate the usefulness of a compound of the invention in the kit for effecting alleviation of the various diseases or disorders recited herein. Optionally, or alternately, the instructional material may describe one or more methods of alleviating the diseases or disorders in a subject. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The term "in situ gelation" refers herein to the thermogelling of chitosan/phosphate gels once the chitosan/phosphate solution is administered within specific sites of a subject. Such sites include, but are not limited to, any tissues, body cavities, muscles, fractures or bone defects, ligaments, cartilages or organs. The thermogelling of the chitosan/phosphate solution is induced by the physiological temperature.

The term 'material", as used herein, refers to synthetic and natural materials such as matrix components. The term "materials and compounds" as used herein, refers to, inter alia, materials, compounds, cells, peptides, nucleic acids, drugs, matrix components, and imaging agents.

The term "metal surface", as used herein, refers to any metal surface, including films, which can be used to deposit or apply polymers or metallic nanoparticles encompassed by the present invention.

A "mold" is a frame or model that shapes the gel system. Gels can be produced in, but are not limited to, glass or plastic-beakers, dishes, tubes or between two plates so as to obtain any expected shape.

The term "nanoparticle" or "particle" refers to a particle of any shape having the size of up to about 100 nanometers.

"Osteogenesis" as used herein refers to bone growth, bone remodeling, and repair of bone due to injury or disease.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The term "prevent," as used herein, means to stop something from happening, or taking advance measures against something possible or probable from happening. In the context of medicine, "prevention" generally refers to action taken to decrease the chance of getting a disease or condition.

A "prophylactic" treatment is a treatment administered to a subject who does not exhibit signs of a disease or injury or exhibits only early signs of the disease or injury for the purpose of decreasing the risk of developing pathology associated with the disease or injury.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

A "reversibly implantable" device is one which may be inserted (e.g. surgically or by insertion into a natural orifice of the animal) into the body of an animal and thereafter removed without great harm to the health of the animal.

A "sample," as used herein, refers to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest.

As used herein, "scaffold" refers to a supporting framework, such as one for bone or tissue growth, either in vivo or in vitro.

The term "skin," as used herein, refers to the commonly used definition of skin, e.g., the epidermis and dermis, and the cells, glands, mucosa, and connective tissue which comprise the skin.

The terms "solid support", "surface" and "substrate" are used interchangeably and refer to a structural unit of any size, where said structural unit or substrate has a surface suitable for immobilization of molecular structure or modification of said structure and said substrate is made of a material such as, but not limited to, metal, metal films, glass, fused silica, synthetic polymers, and membranes.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. "Standard" can also refer to an "internal standard", such as an agent or compound which is added at known amounts to a sample and which is useful in determining such things as purification or recovery rates when a sample is processed or subjected to purification or extraction procedures before a marker of interest is measured. Internal standards are often but are not limited to, a purified marker of interest which has been labeled, such as with a radioactive isotope, allowing it to be distinguished from an endogenous substance in a sample.

A "subject" of diagnosis or treatment is a mammal, including a human.

As used herein, a "subject in need thereof" is a patient, animal, mammal, or human, who will benefit from the method of this invention.

A "surface active agent" or "surfactant" is a substance that has the ability to reduce the surface tension of materials and enable penetration into and through materials.

Before the present compositions and methods are described, it is to be understood that this invention is not limited to the particular processes, compositions, or methodologies described, as these may vary.

The term "symptom," as used herein, refers to any morbid phenomenon or departure from the normal in structure, function, or sensation, experienced by the patient and indicative of disease. In contrast, a sign is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "thermal injury" is used interchangeably with "thermal burn" herein.

A "thermal-sensitive" gel system undergoes a phase transition when induced by temperature.

As used herein, "thermo-gelling" refers to the formation of a colloidal gel from solution as temperature increases.

The term "three-dimensional" refers to the fact that the chitosan solution is simultaneously gelled and shaped by the mold wherein the solution was initially poured.

"Tissue" means (1) a group of similar cells united to perform a specific function; (2) a part of an organism consisting of an aggregate of cells having a similar structure and function; or (3) a grouping of cells that are similarly characterized by their structure and function, such as muscle or nerve tissue.

The term "tissue injury-associated decreased blood flow", as used herein, refers to the decrease in blood flow which occurs following an injury, such as a thermal injury, to a tissue. The decrease in blood flow includes, but is not limited to, decreased volume, rate, stasis, or sludging. One of ordinary skill in the art will appreciate that there are multiple parameters which can be used as measures or signs of decreased blood flow, as well as multiple techniques to determine decreased blood flow.

The term "topical application," as used herein, refers to administration to a surface, such as the skin. This term is used interchangeably with "cutaneous application" in the case of skin. A "topical application" is a "direct application".

By "transdermal" delivery is meant delivery by passage of a drug through the skin or mucosal tissue and into the bloodstream. Transdermal also refers to the skin as a portal for the administration of drugs or compounds by topical application of the drug or compound thereto. "Transdermal" is used interchangeably with "percutaneous."

As used herein, the term "treating" may include prophylaxis of the specific injury, disease, disorder, or condition, or alleviation of the symptoms associated with a specific injury, disease, disorder, or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease. "Treating" is used interchangeably with "treatment" herein.

As used herein "wound" or "wounds" may refer to any detectable break in the tissues of the body, such as injury to skin or to an injury or damage, or to a damaged site associated with a disease or disorder. Although the terms "wound" and "injury" are not always defined exactly the same way, the use of one term herein, such as "injury", is not meant to exclude the meaning of the other term.

CHEMICAL DEFINITIONS

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from two to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from two to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. "Optionally substituted aryl" includes aryl compounds having from zero to four substituents, and "substituted aryl" includes aryl compounds having one or more substituents. The term ($C_5$-$C_8$ alkyl)aryl refers to any aryl group which is attached to the parent moiety via the alkyl group.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "heterocyclic group" refers to an optionally substituted mono- or bicyclic carbocyclic ring system containing from one to three heteroatoms wherein the heteroatoms are selected from the group consisting of oxygen, sulfur, and nitrogen.

As used herein the term "heteroaryl" refers to an optionally substituted mono- or bicyclic carbocyclic ring system having one or two aromatic rings containing from one to three heteroatoms and includes, but is not limited to, furyl, thienyl, pyridyl and the like.

A "meroxapol" is polyoxypropylene-polyoxyethylene block copolymer with the general formula HO($C_3H_6O$)$_a$($C_2H_4O$)$_b$($C_3H_6O$)$_a$H. It is available in different grades. Each meroxapol name is followed by a code number according to the average numerical values of the respective monomers units denoted by "a" and "b". As used herein, the term "optionally substituted" refers to from zero to four substituents, wherein the substituents are each independently selected. Each of the independently selected substituents may be the same or different than other substituents.

A "poloxamer" is a nonionic polyoxyethylene-polyoxypropylene block co-polymer with the general formula HO($C_2H_4O$)$_a$($C_3H_6O$)$_b$($C_2H_4O$)$_a$H. It is available in different grades, which vary from liquids to solids. Each poloxamer name is followed by a code number according to the average numerical values of the respective monomers units denoted by "a" and "b".

A "poloxamine" is a polyoxyethylen-polyoxypropylene block copolymer of ethylene diamine with the general formula [HO($C_2H_4O$)$_a$($C_3H_6O$)$_b$$C_3H_6$]$_2$NCH$_2$CH$_2$N—[$C_3H_6$(OC$_3H_6$)$_b$(OC$_2H_4$)$_a$OH]$_2$. It is available in different grades. Each poloxamine name is followed by a code number according to the average numerical values of the respective monomers units denoted by "a" and "b".

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

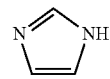

is understood to represent a mixture of the structures:

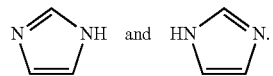 [SMILES: c1c[nH]cn1 ; c1c[nH]cn1]

The terminology used herein is for the purpose of describing the particular versions or embodiments only, and is not intended to limit the scope of the present invention. All publications mentioned herein are incorporated by reference in their entirety.

Embodiments

The present disclosure demonstrates the development of mild and cost effective methods to immobilize metallic nanoparticles on polymeric or metallic substrates.

Metal Substrates

A metal substrate may be a metal or a metal film. In one aspect, the metal or metal film is titanium. In another aspect, the metal is one described below.

Metallic Nanoparticles

The present invention includes nanoparticles comprising metals and composites including, but not limited to, various metals including gold (Au), silver (Ag), platinum (Pt), aluminum (Al), nickel (Ni), iron (Fe), palladium (Pd), titanium (Ti), scandium (Sc), vanadium (V), chromium (Cr), magnesium (Mg), manganese (Mn), cobalt (Co), copper (Cu), zinc (Zn), yttrium (Y), zirconium (Zr), niobium (Nb), molybdenum (Mo), technetium (Tc), ruthenium (Ru), cadmium (Cd), lutetium (Lu), hafnium (Hf), tungsten (W), rhenium (Re), osmium (Os), iridium (Ir), tantalum (Ta), rhodium (Rh), rare-earth metals ytterbium (Yb), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutecium (Lu), and alloys thereof. Preferred metal oxides particles include particles of MgO, SrO, BaO, CaO, TiO$_2$, ZrO$_2$, FeO, V$_2$O$_3$, Y$_2$O$_5$, Mn$_2$O$_3$, Fe$_2$O$_3$, NiO, CuO, Al$_2$O$_3$, SiO$_2$, ZnO, Ag$_2$O, TiSiO$_{0.4}$, ZrSi$_{0.4}$, rare-earth metal oxides, the corresponding hydroxides of the foregoing, particles and quantum dots of semiconducting materials (Si, CdSe, CdSe/CdS, CdSe/ZnSe, PbS, PbSe, ZnS, GaSb, GaAs, InAs), ceramic nano-particles, and mixtures thereof. Suspensions of nanoparticles and nanoscale powders of various compositions can be produced using different methods known in the art and are encompassed by the present invention (see Golovlev et al., U.S. Pat. Pub. 2008/0050842).

Some illustrative but not exhaustive lists of manufacturing methods include precipitation, hydrothermal processing, combustion, arcing, template synthesis, milling, sputtering and thermal plasma taught by Yadav and Pfaffenbach in US. Pat. App. Nos. 20050274447 and 20050063889, and by Reed et al., in U.S. Pat. No. 6,976,647, each of these patents and publications is herein incorporated by reference in its entirety and specifically for description of various methods of manufacturing nano-particles and methods and instruments for milling and reconstituting powders of nano-particles from solid composites.

One aspect of the present invention relates to osteogenic devices, and more specifically to synthetic implants which induce osteogenesis in vivo in mammals, including humans. The invention therefore encompasses metal films and substrates as described herein, as well as such films and substrates further comprising cells. Non-synthetic matrix proteins like collagen, glycosaminoglycans, and hyaluronic acid, which are enzymatically digested in the body, are useful for delivery to bone areas (see U.S. Pat. Nos. 4,394,320; 4,472,840; 5,366,509; 5,606,019; 5,645,591; and 5,683,459) and are suitable for use with the present invention.

Other implantable media and devices can be used to assist, or as supplements to, the use of metal films and substrates for delivery of the cells of the invention in vivo. These include, but are not limited to, sponges, such as those from Integra, fibrin gels, scaffolds formed from sintered microspheres of polylactic acid glycolic acid copolymers (PLAGA), and nanofibers formed from native collagen, as well as other proteins. The cells of the present invention can be further combined with demineralized bone material, growth factors, nutrient factors, pharmaceuticals, calcium-containing compounds, anti-inflammatory agents, antimicrobial agents, or any other substance capable of expediting or facilitating bone growth.

Examples of osteoinductive factors suitable for use with the compositions of the present invention include demineralized bone particles, a Bone Morphogenetic Protein, an osteoinductive extract of demineralized bone matrix, or a combination thereof.

In one aspect, the metal substrates and films of the present invention are useful for growing cells. In one aspect, they support the proliferation and differentiation of cells selected from the group consisting of stem cells, pluripotent stem cells, committed stem cells, embryonic stem cells, adult stem cells, bone marrow stem cells, bone marrow-derived stem cells, adipose stem cells, umbilical cord stem cells, dura mater stem cells, precursor cells, differentiated cells, osteoblasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, normal cells, cancer cells, Schwann cells, and neurons.

Maintaining cells in culture refers to feeding with the appropriate growth medium when necessary, passaging the cells when necessary, etc.

Other materials may also be added to the metal films and substrates, in addition to metal nanoparticles such as silver nanoparticles. These may be attached to the substrate, or in the case of administration to a subject, they can be added at the same time or before or after the metal film or substrate is administered. Compounds and substances that can provide favorable matrix or mesh characteristics also include drugs and other substances that can produce a therapeutic or other physiological effect on cells and tissues within or surrounding an implant. Any substance may be used. Several preferred embodiments include use of any therapeutic molecule including, without limitation, any pharmaceutical or drug. Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

Other preferred embodiments involve the use of growth factors, including more than one growth factor, as described herein.

Other molecules useful as compounds or substances in the present invention include, but are not limited to, growth hormones, leptin, leukemia inhibitory factor (LIF), tumor necrosis factor alpha and beta, endostatin, angiostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18.

Embodiments involving amino acids, peptides, polypeptides, and proteins may include any type of such molecules of any size and complexity as well as combinations of such molecules. Examples include, but are not limited to, structural proteins, enzymes, and peptide hormones. These compounds can serve a variety of functions. In some embodiments, the matrix may contain peptides containing a sequence that suppresses enzyme activity through competition for the active site. In other applications, antigenic agents that promote an immune response and invoke immunity can be incorporated into a construct.

For substances such as nucleic acids, any nucleic acid can be present. Examples include, but are not limited to deoxyribonucleic acid (DNA), ent-DNA, oligonucleotides, aptamers, and ribonucleic acid (RNA). Embodiments involving DNA include, but are not limited to, cDNA sequences, natural DNA sequences from any source, and sense or anti-sense oligonucleotides. For example, DNA can be naked (e.g., U.S. Pat. Nos. 5,580,859; 5,910,488) or complexed or encapsulated (e.g., U.S. Pat. Nos. 5,908,777; 5,787,567). DNA can be present in vectors of any kind, for example in a viral or plasmid vector. In some embodiments, nucleic acids used will serve to promote or to inhibit the expression of genes in cells inside and/or outside the electroprocessed matrix. The nucleic acids can be in any form that is effective to enhance uptake into cells.

Substrates with Nanoparticles

When immobilization of the polymers or the metal particles on the surface has been completed, an additional step of blocking the surface of the solid support can be performed. Blocking prevents non-specific binding of target molecules to the solid support. The blocking also can be used to allocate specific chemical groups on the surface for maintaining desirable positive or negative net surface charge on the substrate surface. Different reagents can be used to block or cap an activated solid support, whereby blocking agents couple and block residual active sites and essentially eliminate said sites from non-specific binding of target biopolymers. Common blocking or capping agents can include glycine, ethanolamine, tris(hydroxymethyl)aminomethane, mercaptoethanol, mercaptoethylamine, cysteine, acetic anhydryde, succinic anhydride, albumine, sodium borohydride, ammonium chloride, sodium acrylate, etc. Maintaining desirable electric charge on the surface can be achieved by using poly-L-lysine, anionic and cationic polymers, for instance, PDDA, amino- and mercapto-silane derivatives, etc. One of ordinary skill in the art will understand if there is a need to adjust concentration and time to optimize blocking treatment to a specific type of chemistry used to activate the solid support.

Polymers, Including Surface Active Copolymers

The present invention also relates to the use of surface active copolymers, including, but not limited to poloxamers. The formulations of the invention may comprise additional therapeutic agents, for example, antimicrobial agents to prevent infection, growth factors or hormones to enhance healing, drugs to treat inflammation, or anesthetics to decrease pain. The present invention encompasses compositions and methods for preparing surface active copolymer compositions comprising metallic nanoparticles.

According to one embodiment, a poloxamer such as poloxamer-188 (Pluronic F68) is the base compound of the composition of the invention. A poloxamer has the special ability to thicken at higher temperatures (such as body temperature) and liquefy at cooler temperatures (cool rinse water for example). The thickness, or viscosity, varies depending on the amount or concentration of surface active copolymer used. These properties enable it to remain resident at tissue surfaces at body temperature but also enable it to be easily removed away with cool water. Preferred surface active copolymers are those which are biocompatible. In addition, dilutions of surface active copolymers such as Poloxamer-188 (Pluronic F68) are very biocompatible.

Disclosed herein are formulations of poloxamers or other surface active agents for topical delivery to injured and diseased tissues and their ability to inhibit the decreased blood flow associated with the injuries, diseases, and disorders described herein. The compounds of the invention can inhibit decreased blood flow by influencing blood flow characteristics such as flow rate, stasis, and sludging.

The invention includes a therapeutic composition comprising at least one surface active copolymer at about 1%-65% w/w. The therapeutic compositions of the invention may be formulated, for example, as liquids or as stable gels.

The therapeutic compositions of the invention have use in treatment of exposed soft tissue or various injuries, for example, thermal injuries, venous stasis ulcers, diabetic wounds, skin grafts, tissue flaps, microvascular surgery, pressure ulcers.

The route of administration can vary depending on the formulation of the pharmaceutical composition being administered as well as on the site of injury, disease, or disorder being treated. The present invention encompasses any useful means of topical administration of the pharmaceutical compositions of the invention to treat the injuries, diseases, and disorders encompassed by the methods of the invention. In one aspect, the compounds are administered via routes, including, but not limited to, direct, topical, cutaneous, mucosal, nasal, inhalation, oral, and ophthalmic. The means for the administration includes, but is not limited to, a dressing material, extruder, aerosol, spray delivery, iontophoresis, a patch, and a transdermal patch.

The present invention further provides for administration of a compound or additional therapeutic agent of the invention as a controlled-release formulation.

The dosage of the active compound(s) being administered will depend on the condition being treated, the particular compound, and other clinical factors such as age, sex, weight, and health of the subject being treated, the route of administration of the compound(s), and the type of composition being administered (gel, liquid, solution, suspension, aerosol, ointment, lotion, cream, paste, liniment, etc.). It is to be understood that the present invention has application for both human and veterinary use.

The invention further encompasses administration of the pharmaceutical compositions of the invention at different times before and after an injury or surgical procedure, as well as varying the optional additional therapeutic agents and the surface active copolymers.

Examples of poloxamers include poloxamer-101, -105, -105 benzoate, -108, -122, -123, -124, -181, -182, -182 dibenzoate, -183, -184, -185, -188, -212, -215, -217, -231, -234, -235, -237, -238, -282, -284, -288, -331, -333, -334, -335, -338, -401, -402, -403, and -407. In one aspect, the poloxamer is poloxamer-188. In another aspect, the poloxamer is poloxamer-407.

In one embodiment, the pharmaceutical composition of the invention comprises PluroGel™ (PluroGen, Annapolis, Md.).

In one embodiment, at least one of the surface active copolymers is a meroxapol. Exemplary meroxapols include, but are not limited to, meroxapol 105, 108, 171, 172, 174, 178, 251, 252, 254, 258, 311, 312, and 314.

In one embodiment, at least one of the surface active copolymers is a poloxamine. Exemplary poloxamines include, but are not limited to, poloxamine 304, 504, 701, 702, 704, 707, 901, 904, 908, 1101, 1102, 1104, 1301, 1302, 1304, 1307, 1501, 1502, 1504, and 1508.

In one embodiment, the therapeutic composition is formulated as a liquid or stable gel. The copolymer size may range, for example, from an $M_n$ of about 600 to about 20,000. In another aspect, the copolymer size may range, for example, from an $M_n$ of about 1,000 to about 10,000.

In another embodiment, the present invention encompasses a composition comprising a poloxamer at about 0.1% to about 85% w/w, or about 1% to about 65%, or about 1% to about 50%, or about 5% to about 40%, or about 10% to about 40%. Other surface active copolymers can be used at these concentrations as well.

The surface active copolymers may be prepared at different temperatures depending on the type of formulation being prepared, the route of administration, the site of administration, etc. In one aspect, the surface active copolymer is prepared at a temperature ranging from about 0° F. to about 70° F. In another aspect, the surface active copolymer is prepared at a temperature ranging from about 5° F. to about 50° F. In yet another aspect, the surface active copolymer is prepared at a temperature ranging from about 10° F. to about 40° F.

The composition may further comprise an effective amount of at least one additional therapeutic agents which may be useful for the type of injury, disease, or disorder being treated. Additional therapeutic agents include, but are not limited to, anesthetic, analgesic, antimicrobial, steroid, growth factor, cytokine, and anti-inflammatory agents. Useful anesthetic agents include benzocaine, lidocaine, bupivocaine, dibucaine, mepivocaine, etidocaine, tetracaine, butanilicaine, and trimecaine.

In another aspect, the agent is at least one analgesic. In yet another aspect, the agent is an additional therapeutic drug.

In a further aspect, the additional therapeutic agent is an antimicrobial agent. In one aspect, the antimicrobial agent is an antibacterial agent. In another aspect, the antimicrobial agent is an antifungal agent. In yet another aspect, the antimicrobial agent is an antiviral agent. Antimicrobial agents useful in the practice of the invention include, but are not limited to, silver sulfadiazine, Nystatin, Nystatin/triamcinolone, Bacitracin, nitrofurazone, nitrofurantoin, a polymyxin (e.g., Colistin, Surfactin, Polymyxin E, and Polymyxin B), doxycycline, antimicrobial peptides (e.g., natural and synthetic origin), Neosporin (i.e., Bacitracin, Polymyxin B, and Neomycin), Polysporin (i.e., Bacitracin and Polymyxin B). Additional antimicrobials include topical antimicrobials (i.e., antiseptics), examples of which include silver salts, iodine, benzalkonium chloride, alcohol, hydrogen peroxide, and chlorhexidine. It may be desirable for the antimicrobial to be other than Nystatin.

In another aspect, the agent is selected from aspirin, pentoxifylline, and clopidogrel bisulfate, or other angiogenic, or a rheologic active agent.

In one embodiment, the present invention encompasses a method of treating a site of injury on a subject comprising topically administering a poloxamer to the subject in an amount effective to improve blood flow at the site of injury. In one aspect, the blood flow is microvascular blood flow.

Depending on such things as the type of formulation being prepared, the location to which it is to be applied, and the type of injury, disease, or disorder being treated, other agents can be added to the formulation. For example, other additives may include, a moisturizer, a humectant, a demulcent, oil, water, an emulsifier, a thickener, a thinner, an additional surface active agent, a fragrance, a preservative, an antioxidant, a hydrotropic agent, a chelating agent, a vitamin, a mineral, a permeation enhancer, a cosmetic adjuvant, a bleaching agent, a depigmentation agent, a foaming agent, a conditioner, a viscosifier, a buffering agent, and a sunscreen.

In one aspect, the microvasculature has a diameter ranging from about 5 µm to about 100 µm. In another aspect, the vessels have a diameter from about 10 µm to about 50 µm. Vessels encompassed by the treatment of the invention include, but are not limited to, capillaries, arterioles, and venules.

In another embodiment, the present invention provides a method of treating a site of injury on a subject comprising topically administering a poloxamer to the patient in an amount effective to reduce inflammation at the site of injury.

Compositions and Formulations of the Base Surface Active Copolymer

The invention encompasses the preparation and use of pharmaceutical compositions comprising as an active ingredient a compound useful for treatment of decreased blood flow associated with injuries and diseases disclosed herein. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art. The present invention further contemplates the use of more than one active ingredient.

In one embodiment, at least two different surface active copolymers are used. In one aspect, at least three different surface active copolymers are used. These combinations may include, for example, one or more poloxamers, one or more meroxapols, and one or more poloxamines.

Compositions of this type are described in U.S. Pat. No. 5,635,540 (Edlich et al.), the contents of which are incorporated herein by reference.

Examples of temperature ranges for preparation include, but are not limited to, from about −20° C. to about 15° C., in another aspect from about −18° C. to about 8° C., and in another aspect, from about −15° C. to about 5° C. These ranges also encompass about 0° F. to about 60° F. One of ordinary skill in the art will understand that the temperatures of preparation can be adjusted based on various criteria, such as the surface active copolymer being used, the amount or concentration being used, the type of formulation being prepared for administration, etc.

In one embodiment of the invention, the poloxamer base comprises 80% polyoxyethylene units and 20% polyoxypropylene units.

One of ordinary skill in the art will appreciate that the formulations, method of preparation, and amount of surface active copolymer used may vary, depending on the type or location of the site to be treated. For example, in one embodiment, a poloxamer, such as poloxamer-188, is mixed with water at a ratio of from 1:0.8 to 1.2 w/w. This ratio can be varied. This combination may be mixed until the powder has been wetted. The mixture may then be placed in a freezer or refrigerator and cooled, preferably for at least 4 hours. While cooling, the mixture will undergo phase transition to a liquid, as demonstrated by Edlich et al. (U.S. Pat. No. 5,635,540). The mixture is then removed from the freezer and warmed to room temperature. Pharmaceutical agents such as antimicrobials and anesthetics can be added at this point, as demonstrated by Edlich et al. (U.S. Pat. No. 5,635,540).

The poloxamer base used in preparing the topical preparation of the present invention is a polyoxyalkylene based polymer based on ethylene oxide and propylene oxide and comprises a series of closely related block polymers that may generally be classified as polyoxyethylene-polyoxypropylene condensates terminated in primary hydroxyl groups. They are formed by the condensation of propylene oxide onto a propylene glycol nucleus followed by condensation of ethylene oxide onto both ends of the polyoxypropylene base. The polyoxyethylene hydrophilic groups on the ends of the molecule are controlled in length to constitute anywhere from 10% to 90% by weight of the final molecule.

The compositions of the present invention may comprise one or more co-additives (e.g., solvent such as water). In one aspect, the concentration of a surface active copolymer (e.g., poloxamer 188) is about 0.01 to about 99.99% w/w. In another aspect, it is about 1 to about 90%. In yet another aspect, it is about 10 to about 80%. In a further aspect, it is about 20% to about 70%. In another aspect, it is about 50%. In a further aspect, it is about 5%.

In another embodiment, a formulation of the invention can be impregnated in a dressing material (or otherwise contained or encompassed by the dressing material). The dressing material is a pharmaceutically acceptable fabric. It can be, for example, gauze or any other type of medical fabric or material that can be used to cover a wound and/or to keep a therapeutic agent or composition in contact with a patient.

Chitosan and Carboxymethyl Chitosan

The present invention further encompasses the use of a thermo-gelling chitosan solution that remains liquid at lower temperatures but gels at higher temperatures and requires a lower concentration of cross-linking agents, to which metals such as silver can be added. The present invention relates to a biocompatible thermo-gelling solution of chitosan and inorganic salts and methods for the preparation of and the use of such a solution. In one aspect, the invention encompasses the use of carboxymethyl chitosan.

Chitosan is an N-deacetylated derivative of chitin which is the structural component of crustacean shells and fungal cell walls, and is obtained at a low cost from sea-food processing (Chitin: Fulfilling a Biomaterials Promise: Eugene Khor, Elsevier, Oxford, UK, 2001). The structure of chitin and chitosan are similar to cellulose where, carbon-2 of the cellulose has acetamide or amino groups, for chitin and chitosan respectively. Chitosan is an inert, hydrophilic, biocompatible, and biodegradable polymer and hence are attractive candidates for biomedical and pharmaceutical applications. Chitosan is currently investigated for various applications such as topical ocular application, as a bioadhesive polymer, penetration enhancer by opening epithelial tight junctions and as wound dressing (Berger, et al., European Journal of Pharmaceutics and Biopharmaceutics 57 (2004) 19-34).

Various chemically modified chitosan derivatives with unique properties have been developed (Hitoshi et al., Prog. Polym. Sci. 29 (2004) 887-908). The excellent biocompatibility of chitosan, combined with its enzymatic biodegradability, makes chitosan an excellent candidate for various in vivo applications. In addition, the low cost of chitosan and its wide availability as a natural waste product, makes chitosan a very attractive polymer for wide range of applications.

Chitosan has been extensively investigated for developing hydrogels with unique properties, due to the hydrophilicity of the base polymer, and the availability of active cross-linkable groups along the polymer chain. These chitosan hydrogels were found to be excellent candidates for a variety of applications, including, controlled release of bioactive/drug molecules, as cell encapsulation matrices, and as tissue engineering scaffolds. Chemical or covalent cross-linking of chitosan making use of mainly the active amino groups along the polymer chain and ionic cross-linking making use of the cationic nature of chitosan aqueous acid solutions, have been extensively investigated for developing hydrogels for various applications.

The different chemical cross-linking agents reported for chitosan include dialdehydes such as glutaraldehyde, diethyl squarate, oxalic acid, and genipin. Apart from these small molecules, functionalized biopolymers such as poly(ethylene glycol diacrylate), oxidized cyclodextrin, telechelic-PVA, PEG dialdehydes and scleroglucan have also been investigated.

In addition to covalent cross-linking, polyelectrolyte complexes of chitosan with a wide range of anionic polymers mainly chitosan alginate system have been extensively investigated for developing drug delivery systems and porous scaffolds for tissue engineering and wound dressings.

Ionic cross-linking of chitosan has been extensively investigated, because it is a simple and mild process with no auxiliary catalyst requirements, and such a procedure has important ramifications for biomedical applications. Metallic anions such as Mo(VI) and Pt(II) have been extensively investigated for ionic cross-linking Various anions such as sulfates, citrates, oxalates, polyphosphates, and also calcium phosphate, have been tested for the ability to form ionically cross-linked gels with chitosan. All of these ions induce the formation of pure ionic cross-linking, where the chitosan solution instantaneously becomes a gel in the presence of these ions, due to the spontaneity of the ionic reactions.

Recently a novel temperature and pH sensitive gelling system was developed using chitosan in the presence of β-glycerophosphate. In addition to β-glycerophosphate, corresponding sulfates and monosaccharide derivatives were found to exhibit the characteristic properties of β-glycerophosphate (Chemte et al., U.S. Pat. No. 6,344,488; Chemte et al., Biomaterials 21 (2000) 2155-2161; Ruel-Gariepy et al., European Journal of Pharmaceutics and Biopharmaceutics, 57 (2004) 53-63; Ruel-Gariepy et al., J Controlled Release. 82 (2002) 373-383; Molinaro et al., Biomaterials 23 (2002), 2717-2722).

Injectable in situ forming hydrogels are receiving considerable attention for a variety of biomedical applications such as sustained drug delivery, cell encapsulation and as scaffolds for tissue engineering (Tae et al., Biomaterials, 26, 5259-66, 2005). An injectable system offers several advantages including conformal matching of the implant to complex tissue shapes, delivery of large volumes of implant via minimally invasive surgery, improved patient compliance and comfort, and allows for the delivery of sensitive biomolecules and living cells because it is a gentle process. In situ forming hydrogels are potential candidates specifically for developing sustained delivery vehicles for therapeutic proteins with short half lives.

Various materials have been investigated for the development of injectable hydrogel systems based on non-degradable synthetic polymers such as poloxamers, N-isopropylacrylamide and a variety of degradable natural polymers (Hatefi and Amsden, J. Control Rel., 80:9-28, 2002). One of the most extensively investigated natural polymers for hydrogel development is chitosan. Chitosan is an N-acetylated derivative of the natural polymer Chitin. Chitin is the structural component of crustacean shells and fungal cell walls and is the second most abundant natural polymer. Due to the excellent biocompatibility and enzymatic degradability of chitosan, hydrogels based on chitosan have been found to be excellent candidates for a variety of medical and pharmaceutical applications (Berger et al., Eur. J. Pharm. BioPharm., 57:19-34, 2004).

Different types of cross-linking agents have been investigated for developing chitosan hydrogels. These include chemical cross-linking using various aldehydes, ionic cross-linking using various anions, and polyelectrolyte complexes using anionic polymers. Recently much research has gone into developing stimuli sensitive injectable systems based on chitosan. It has been found that addition of certain polyol counterionic monohead salts such as β-glycerophosphate can lead to the development of temperature and pH sensitive gelling systems (Chemte et al, Biomaterials, 21:2155-61, 2000). Grafting poly(ethylene glycol) of appropriate molecular weight to chitosan has been shown to act as a thermogelling system (Bhattarai et al., J. Control Rel. 103:609-624).

The thermo-gelling solution of the present invention can be prepared by mixing chitosan solution in very dilute acetic acid with appropriate amounts of inorganic salts, such as phosphate or sulfate salt powder or solution, at a low temperature, such as between about 0° C. and about 4° C., with rapid stirring. The addition of salt powder or solution rapidly increases the pH of the acidic chitosan solution to a pH between about 6.0 and about 8.0.

Chitosan solutions are known generally to precipitate instantaneously as the pH of the solution is raised to above about 6.0. However, it has been found that in the presence of the inorganic phosphate described here the chitosan remains in solution even at about neutral pH between about 7.0 and about 7.2, so long as the solution is maintained at a temperature below about 10° C. When chitosan solutions are mixed with appropriate inorganic phosphates at low temperatures and are then heated to near-physiological temperatures, such as about 37° C., the solutions gel. The thermo-gelling solution of the present invention forms a gel within a temperature range from about 30° C. to about 50° C. This temperature range is not intended to be exclusive of other temperatures where the thermo-gelling solution of the present invention may form a gel. On the other hand, the thermo-gelling solution of the present invention may also gel at temperatures above or below the temperature range from about 30° C. to about 50° C. However, the thermo-gelling solution of the present invention certainly gels at a temperature within this range, which encompasses near-physiological temperatures.

The time of gelling has been found to depend on several factors including the concentration of the inorganic phosphate salts, concentration of chitosan solution and concentration of aqueous acetic acid solution. The final pH of the solution also correlates with the gelling time of the present thermo-gelling system. In one aspect, the pH of the final solution should be between about 6.0 and about 8.0. For efficiently gelling chitosan solutions, the final pH of the solution has been found to be equal to or higher than 6.8.

The time of gelling has been found to be independent of storage time and dilution of the solution. The thermo-gelling solution of the present invention has been found to be stable when stored over time at temperatures below about 5° C. Dilution of the thermo-gelling chitosan-inorganic salt solution has also been found not to significantly affect the gelling time of the solution. Because dilution does not significantly affect gelling times, thereto-gelling systems may be developed which will enable the formation of gels of different strengths and water contents for various applications. It has been found that the strength of the gels and the water content of the gels can be varied by varying the concentration of the inorganic phosphate salts added or by diluting the chitosan-inorganic phosphate mixture with distilled water, phosphate buffer, or cell culture media. In one embodiment, the present invention provides a method to develop a thermo-gelling system having different water content and gel strength depending on the planned application. Such methods and compositions for using chitosan are described in, for example, International Patent Publication WO 2007/087350 (Laurencin et al.) published Aug. 2, 2007.

The present invention relates to the preparation of a chitosan solution having neutral pH, which can undergo thermogelation at about a physiological temperature and physiological pH. In one aspect, the solution undergoes gelation at near or above physiological temperature. In one aspect, the thermogelling or thermosetting solution can be prepared by mixing chitosan solution in very dilute acetic acid with appropriate amounts of inorganic phosphate salt powder or solution at 0-4° C. with rapid stirring. The addition of salt powder or solution rapidly increases the pH of the acid chitosan solution to near neutral pH. Chitosan solutions are known to precipitate instantaneously as the pH of the solution is raised to above ~6.0. However, it has been found that in the presence of the inorganic phosphate described here, the chitosan remains in solution even at neutral pH (~pH 7.0-7.2). When a chitosan solution of the invention is mixed with appropriate inorganic phosphates at low temperature and heated to near physiological temperature (37° C.) or above, the solutions gel. The time required for gelling to occur has been found herein to depend on several factors, including the concentration of the inorganic phosphate salts, concentration of chitosan solution, and the concentration of aqueous acetic acid solution. The final pH of the solution also correlates to regulation of the present thermogelling system. In one aspect, in an efficient gelling chitosan solution, the final pH of the solution should be approximately at least about 6.8.

In one embodiment, the strength of the gels and the water content of the gels can be varied by varying the concentration of the inorganic phosphate salts added, or by diluting the chitosan-inorganic phosphate mixture with distilled/deionized water, phosphate buffer, weak acid-base, or using cell culture medium.

In one embodiment of the invention, thereto-gelling composite systems are useful as, injectable compositions for various applications. The compositions can be developed mixing insoluble solid particulates with a chitosan-inorganic phosphate mixture, or by mixing water-soluble polymer solutions with chitosan-inorganic phosphate mixture.

In one embodiment, the invention provides a non-toxic, biodegradable, biocompatible and rapidly curing system at physiological temperature to use in a clinical or operating room setting.

In one embodiment, the invention provides a temperature induced rapidly curing two component solution which can solidify into a biodegradable gel for various applications.

In one embodiment, the invention provides a temperature induced rapidly curing system which can be used to develop novel blends or composite systems.

In one embodiment, the invention provides a temperature induced rapidly gelling polymer system as an injectable matrix for the controlled and prolonged delivery of drugs, growth factors, therapeutic proteins and peptides.

In one embodiment, the invention provides a temperature induced rapidly gelling polymer system as an injectable plug for therapeutic embolization and chemoembolization.

In one embodiment, the invention provides a method for preparing thermogelling chitosan solutions with variable gelation times. In one aspect, the gelation times are as short as about several minutes. In another aspect, the gelation times are from about 30 minutes to about several hours. In yet another aspect of the invention, gelation times range from about several hours to about 24 to 36 hours.

In one embodiment, the invention provides a temperature induced rapidly gelling polymer system as an injectable scaffold for various tissue engineering applications.

In one embodiment, the invention provides a temperature induced rapidly gelling polymer system as an injectable cell encapsulation system for various applications.

In one embodiment, the invention provides variable gelling time from a few minutes to a few hours depending on the kind of application the material is targeted.

In one embodiment, the invention provides a method to develop hydrogel system having different water content and gel strength depending on the kind of application the material is targeted.

In one embodiment, the invention provides a method to develop cross-linked systems having different architecture such as foams, spheres, fibers.

In one embodiment, the invention provides novel delivery systems. In one aspect, the present invention provides methods and composition for delivering cells, chondrocytes, stem cells, genes, matrix materials, drugs, proteins, and chemicals. Delivery of bioactive molecules such as nucleic acid molecules encoding a protein can be significantly enhanced by immobilization of the bioactive molecule in a composition of the invention adjacent to the cells where delivery is desired.

In one embodiment, the invention provides methods for administering novel delivery systems. In one aspect, the novel delivery systems are administered to treat diseases, disorders, and conditions in subjects in need thereof. In one aspect, the invention is useful for treating a musculoskeletal-associated disease or disorder. Musculoskeletal-associated diseases or disorders are described herein or are known in the art. In one aspect, the method is useful for enhancing bone repair. In another aspect, the method is useful for treating a bone-associated disease or disorder. In one aspect, treatment of a bone-associated disease or disorder can be done in conjunction with a surgical procedure. In one embodiment, the present invention provides methods and compositions for fabricating three-dimensional structures. In one aspect, the present invention provides various fabrication techniques. One of ordinary skill in the art would appreciate that various fabrication techniques are available to practice the methods of the invention.

In one embodiment, the present invention provides compositions and methods for tissue regeneration. In one aspect, the tissues are selected from the group consisting of bone and spine.

In one embodiment, the compositions and methods of the invention are useful for tissue engineering.

In one embodiment, the compositions and methods of the invention are useful for preparing composites with organic or inorganic components.

In one embodiment, the compositions and methods of the invention are useful in cell and tissue culture systems. In one aspect, the invention provides methods for encapsulating cells.

The skilled practitioner, practicing the invention, could find wide applications for this thermo-gelling solution. Such applications include use as scaffolds for tissue engineering applications, as tissue adhesive, as a wound dressing material, as injectable fillers or composites, and as an injectable solution for controlled and prolonged delivery of drugs, proteins, and growth factors. The invention provides advantages of a workable, flowable, injectable liquid at colder temperatures along with the advantages of a biocompatible viscous gel at higher, physiological temperatures. The teachings of the present invention also overcome limitations of the prior art by providing for simple, mild, and gentle cross-linking agents at lower concentrations than required by the prior art.

In one aspect, the present invention features a solution of chitosan and inorganic salt maintained at a temperature below about 10° C. that forms a gel as the temperature rises to within a temperature range from about 20° C. to about 50° C. In one aspect, the temperature for gelling is from about 30° C. to about 40° C. The thermo-gelling solution has a pH between about 6.0 and about 8.0.

In one embodiment, the thermo-gelling solution comprises a solution of chitosan and inorganic phosphate or sulfate salts. In a preferred embodiment, the thermo-gelling solution comprises a solution of chitosan and ammonium hydrogen phosphate. In one embodiment, the thermo-gelling solution comprises between about 0.05 weight % and about 10.0 weight % chitosan and between about 0.5 weight % and about 2.8 weight % ammonium hydrogen phosphate. In embodiment, the thermo-gelling solution comprises a ratio of chitosan to ammonium hydrogen phosphate between about 1 and about 3.5.

In another embodiment, the thermo-gelling solution is a solution at a pH between about 6.5 and about 7.5. In a more preferred embodiment, the thermo-gelling solution is a solution at a pH between about 6.8 and about 7.3. In a most preferred embodiment, the thermo-gelling solution is a solution at a pH between about 7.0 and about 7.2

In another embodiment, the thermo-gelling solution is a solution maintained at a temperature below about 5° C. In a currently preferred embodiment, the thermo-gelling solution is maintained at a temperature between about 0° C. and about 4° C.

In a further embodiment, the thermo-gelling solution forms a gel as the temperature rises to within a temperature range from about 35° C. to about 45° C. In a more preferred embodiment, the thermo-gelling solution forms a gel within a temperature range from about 35° C. to about 40° C. In a most preferred embodiment, the thermo-gelling solution forms a gel at a temperature of about 37° C.

The invention further encompasses chitosan of varied molecular weights. In one aspect, chitosan from about 20,000 to about 250,000 is encompassed within the methods described herein.

In accordance with the present invention, there is also provided a pharmaceutical composition comprising a thermo-gelling solution of chitosan and inorganic salts and insoluble solid particulates or water-soluble substances. There is also provided a method for administering the pharmaceutical composition comprising injecting or applying the pharmaceutical composition.

In accordance with the present invention, there is also provided a method of preparing a thermo-gelling solution of the present invention, which comprises the steps of (a) dissolving chitosan within an acidic aqueous solution to obtain an aqueous chitosan solution; (b) maintaining the aqueous chitosan solution at a temperature below about 10° C.; and (c) dissolving an inorganic salt in the aqueous chitosan solution to obtain a thermo-gelling solution, wherein the thermo-gelling solution is a solution at pH between about 6.0 and about 8.0 and forms a gel within a temperature range of about 30° C. to about 50° C.

In one embodiment, an inorganic salt includes inorganic phosphate and/or sulfate salts. In a preferred embodiment, an inorganic salt is ammonium hydrogen phosphate.

In another preferred embodiment, the aqueous chitosan solution comprises between about 0.5 weight % and about 3.5 weight % chitosan.

In another preferred embodiment, the thermo-gelling solution is a solution having a concentration between about 0.5 weight % and about 2.8 weight % ammonium hydrogen phosphate. In still another preferred embodiment steps (a), (b), and (c) yield a thermo-gelling solution having a ratio of chitosan to ammonium hydrogen phosphate between about 1 and about 3.5.

In a further embodiment, steps (a), (b), and (c) yield a thermo-gelling solution at pH between about 6.5 and about 7.5. In a more preferred embodiment, steps (a), (b), and (c) yield a thermo-gelling solution at pH between about 6.8 and about 7.3. In a most preferred embodiment, steps (a), (b), and (c) yield a thermo-gelling solution at pH between about 7.0 and about 7.2.

In a further embodiment, the aqueous chitosan solution is maintained below about 5° C. In a currently preferred embodiment, the aqueous chitosan solution is maintained between about 0° C. and about 4° C.

In a still further embodiment, the thermo-gelling solution formed by steps (a), (b), and (c) forms a gel as the temperature rises to within a temperature range from about 35° C. to about 45° C. In a more preferred embodiment, the thermo-gelling solution forms a gel within a temperature range from about 35° C. to about 40° C. In a most preferred embodiment, the thermo-gelling solution forms a gel at a temperature of about 37° C.

In accordance with the present invention there are also provided methods of using the thermo-gelling solution of the present invention. The invention provides a method of delivering the thermo-gelling solution as an injectable scaffold for tissue engineering comprising injecting an effective amount of the thermo-gelling solution.

The invention further provides a method for delivering one or more substances from the group consisting of cells, fibroblasts, chondrocytes, osteogenic cells, stem cells, genes, drugs, proteins, chemicals, bioactive molecules, growth factors, and therapeutic proteins and peptides comprising administering the thermo-gelling solution as an injectable matrix for the delivery of these substances.

The invention still further provides a method for providing the thermo-gelling solution as an injectable plug for therapeutic embolization and chemoembolization comprising injecting the thermo-gelling solution as an injectable plug for therapeutic embolization and chemoembolization.

Therapeutics

The embodiments of the invention can be useful for therapeutic purposes based on the properties of the metal nanoparticles, the silver comprising surfaces, substrates, and compositions themselves, or when additional therapeutic agents are used. For example, several preferred embodiments include use of any therapeutic molecule including, without limitation, any pharmaceutical or drug. These can be added separately to the substrate or composition or in conjunction with the metal being added to the substrate or composition. One of ordinary skill in the art will appreciate that additional therapeutic agents can also be administered to a subject in need thereof separately from the metal nanoparticle comprising surfaces and compositions of the invention.

Additional Therapeutic Agents and Ingredients

The composition of the invention can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; (e) growth factors; (f) cytokines; (g) hormones; and (h) combinations thereof.

In one embodiment, a formulation of the invention contains an antimicrobial agent. The antimicrobial agent may be provided at, for example, a standard therapeutically effective amount. A standard therapeutically effective amount is an amount that is typically used by one of ordinary skill in the art or an amount approved by a regulatory agency (e.g., the FDA or its European counterpart). Antimicrobial agents useful for the invention include those directed against the spectrums of gram positive organisms, gram negative organisms, fungi, and viruses.

According to the topical anesthetic embodiment of the present invention, in one aspect, suitable local anesthetic agents having a melting point of 30° to 70° C. are prilocalne, tetracaine, butanilcaine, trimecaine, benzocaine, lidocaine, bupivocaine, dibucaine, mepivocaine, and etidocaine.

Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

A list of the types of drugs, and specific drugs within categories which are encompassed within the invention is provided below and are intended be non-limiting examples.

Antimicrobial Agents Include:

Silver sulfadiazine, Nystatin, Nystatin/triamcinolone, Bacitracin, nitrofurazone, nitrofurantoin, a polymyxin (e.g., Colistin, Surfactin, Polymyxin E, and Polymyxin B), doxycycline, antimicrobial peptides (e.g., natural and synthetic origin), Neosporin (i.e., Bacitracin, Polymyxin B, and Neomycin), Polysporin (i.e., Bacitracin and Polymyxin B). Additional antimicrobials include topical antimicrobials (i.e., antiseptics), examples of which include silver salts, iodine, benzalkonium chloride, alcohol, hydrogen peroxide, and chlorhexidine.

Analgesic:

Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lomoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propiram Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin.

Antihypertensive:

Aflyzosin Hydrochloride; Alipamide; Althiazide; Amiquinsin Hydrochloride; Amlodipine Besylate; Amlodipine Maleate; Anaritide Acetate; Atiprosin Maleate; Belfosdil; Bemitradine; Bendacalol Mesylate; Bendroflumethiazide; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicomide; Buthiazide: Candoxatril; Candoxatrilat; Captopril; Carvedilol; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Dilevalol Hydrochloride; Diltiazem Malate; Ditekiren; Doxazosin Mesylate; Ecadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydralazine Polistirex; Hydroflumethiazide; Indacrinone; Indapamide; Indolaprif Hydrochloride; Indoramin; Indoramin Hydrochloride; Indorenate Hydrochloride; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Metipranolol; Metolazone; Metoprolol Fumarate; Metoprolol Succinate; Metyrosine; Minoxidil; Monatepil Maleate; Muzolimine; Nebivolol; Nitrendipine; Oformine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Primidolol; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Teludipine Hydrochloride; Temocapril Hydrochloride; Terazosin Hydrochloride; Terlakiren; Tiamenidine; Tiamenidine Hydrochloride; Ticrynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; Zofenoprilat Arginine.

Anti-Inflammatory:

Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Growth Factors

In one embodiment, an effective amount of at least one growth factor, cytokine, hormone, or extracellular matrix compound or protein useful for enhancing wound healing is administered. In one aspect, a combination of these agents is used. In one aspect, growth factors useful in the practice of the invention include, but are not limited to, EGF, PDGF, GCSF, IL6, IL8, IL10, MCP1, MCP2, Tissue Factor, FGFb, KGF, VEGF, PLGF, MMP1, MMP9, TIMP1, TIMP2, TGFβ, and HGF. One of ordinary skill in the art will appreciate that the choice of growth factor, cytokine, hormone, or extracellular matrix protein used will vary depending on criteria such as the type of injury, disease, or disorder being treated, the age, health, sex, and weight of the subject, etc. In one aspect, the growth factors, cytokines, hormones, and extracellular matrix compounds and proteins are human.

Proteins and other biologically active compounds that can be incorporated into, or included as an additive within, a composition comprising compounds of the present invention include, but are not limited to, collagen (including cross-linked collagen), fibronectin, laminin, elastin (including cross-linked elastin), osteopontin, osteonectin, bone sialo-proteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, skeletal growth factor, enzymes, or combinations and biologically active fragments thereof. Adjuvants that diminish an immune response can also be used in conjunction with the composite of the subject invention.

Other molecules useful as compounds or substances in the present invention include, but are not limited to, growth hormones, leptin, leukemia inhibitory factor (LIF), tumor necrosis factor alpha and beta, endostatin, angiostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18. Embodiments involving amino acids, peptides, polypeptides, and proteins may include any type of such molecules of any size and complexity as well as combinations of such molecules.

The present invention encompasses treatment of various injuries, diseases, and disorders. These include, but are not limited to, thermal injury, skin injury, soft tissue injury, non-healing skin wound, burns, acute wound, chronic wound, scrape, cut, incision, laceration, decubitis, pressure ulcer, chronic venous ulcer, venous stasis ulcer, diabetic ulcer, arterial ulcer, radiation ulcer, traumatic wound, open complicated non-healing wound, body piercing, bite wound, insect bite, insect sting, stab wound, gunshot wound, stretch injury, crush wound, compression wound, fracture, sprain, strain, stroke, infarction, aneurism, herniation, ischemia, fistula, dislocation, radiation, surgery, cell, tissue or organ grafting, and cancer.

In one embodiment, the invention provides novel delivery systems. In one aspect, the present invention provides methods and composition for delivering cells, chondrocytes, stem cells, genes, matrix materials, drugs, proteins, and chemicals. Delivery of bioactive molecules such as nucleic acid molecules encoding a protein can be significantly enhanced by immobilization of the bioactive molecule in a composition of the invention adjacent to the cells where delivery is desired.

In one embodiment, the invention provides methods for administering novel delivery systems. In one aspect, the novel delivery systems are administered to treat diseases, disorders, and conditions in subjects in need thereof. In one aspect, the invention is useful for treating a musculoskeletal-associated disease or disorder. Musculoskeletal-associated diseases or disorders are described herein or are known in the art. In one aspect, the method is useful for enhancing bone repair. In another aspect, the method is useful for treating a bone-associated disease or disorder. In one aspect, treatment of a bone-associated disease or disorder can be done in conjunction with a surgical procedure. In one embodiment, the present invention provides methods and compositions for fabricating three-dimensional structures. In one aspect, the present invention provides various fabrication techniques. One of ordinary skill in the art would appreciate that various fabrication techniques are available to practice the methods of the invention.

In one embodiment, the present invention provides compositions and methods for tissue regeneration. In one aspect, the tissues are selected from the group consisting of bone and spine.

In one embodiment, the compositions and methods of the invention are useful for tissue engineering.

In one embodiment, the compositions and methods of the invention are useful for preparing composites with organic or inorganic components.

In one embodiment, the compositions and methods of the invention are useful in cell and tissue culture systems. In one aspect, the invention provides methods for encapsulating cells.

Pharmaceutical Compositions and Delivery Form

The formulations of the invention may be prepared in a variety of forms known in the art, such as liquids, aerosols, or gels. Topical administration of the present formulation can be performed by, for example, hand, mechanically (e.g., extrusion and spray delivery) or as a component of a dressing (e.g., gauze or other wound covering). The administration of the formulation directly by hand to a tissue or biomaterial surface is preformed so as to achieve a therapeutic coating, which may be uniform, alone or in combination with an overlying dressing.

In one embodiment, the administration of the formulation mechanically is performed by using a device that physically pushes the composition onto a tissue or biomaterial surface so as to achieve a therapeutic coating, which may be uniform, alone or in combination with an overlying dressing.

In another embodiment, the formulation can be sprayed onto a tissue or biomaterial surface so as to achieve a therapeutic coating, which may be uniform, alone or in combination with an overlying dressing. When part of a dressing, the formulation is applied so as to achieve a therapeutic coating of the surface, which may be uniform.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 70% (w/w) active ingredient, although the concentration of the active ingredient may be as high as the solubility limit of the active ingredient in the solvent. Formulations for topical administration may further comprise one or more of the additional ingredients described herein.

Those of ordinary skill in the art will be able to identify readily those pharmaceutical agents that have utility with the present invention. Those of ordinary skill in the art will also recognize numerous other compounds that fall within the categories and that are useful according to the invention for treating injuries where reduced blood flow occurs.

The invention encompasses the preparation and use of pharmaceutical compositions comprising a compound useful for treatment of various skin related injuries, trauma, diseases, disorders, or conditions described herein, including burns, wounds, surgical incisions, etc. The invention also encompasses other injuries, trauma, associated diseases and disorders other than those of the skin, including, but not limited to, gum diseases and disorders. Such a pharmaceutical composition may consist of the active ingredient alone, in a form suitable for administration to a subject, or the pharmaceutical composition may comprise at least one active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

An obstacle for topical administration of pharmaceuticals to the skin is the stratum corneum layer of the epidermis. The stratum corneum is a highly resistant layer comprised of protein, cholesterol, sphingolipids, free fatty acids and various other lipids, and includes cornified and living cells. One of the factors that limits the penetration rate (flux) of a compound through the stratum corneum is the amount of the active substance which can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

The compounds of the invention may be administered to, for example, a cell, a tissue, or a subject by any of several methods described herein and by others which are known to those of skill in the art.

The relative amounts of the active ingredient, the pharmaceutically acceptable carrier, and any additional ingredients in a pharmaceutical composition of the invention will vary, depending upon the identity, sex, age, size, and condition of the subject treated and further depending upon the route by which the composition is to be administered.

In addition to the active ingredient, a pharmaceutical composition of the invention may further comprise one or more additional pharmaceutically active or therapeutic agents. Particularly contemplated additional agents include anti-emetics and scavengers such as cyanide and cyanate scavengers.

Controlled- or sustained-release formulations of a pharmaceutical composition of the invention may be made using conventional technology.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Additionally, formulations for topical administration may include liquids, ointments, lotions, creams, gels (e.g., poloxamer gel), drops, suppositories, sprays, aerosols, and powders. Conventional pharmaceutical carriers, aqueous, powder or oily bases, thickeners and the like may be necessary or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or any bio-engineered materials.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

The source of active compound to be formulated will generally depend upon the particular form of the compound. Small organic molecules and peptidyl or oligo fragments can be chemically synthesized and provided in a pure form suitable for pharmaceutical/cosmetic usage. Products of natural extracts can be purified according to techniques known in the art. Recombinant sources of compounds are also available to those of ordinary skill in the art.

In alternative embodiments, the topically active pharmaceutical composition may be optionally combined with other ingredients such as moisturizers, cosmetic adjuvants, antioxidants, chelating agents, bleaching agents, tyrosinase inhibitors, and other known depigmentation agents, surfactants, foaming agents, conditioners, humectants, wetting agents, emulsifying agents, fragrances, viscosifiers, buffering agents, preservatives, sunscreens, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art. The compositions of this invention may also contain active amounts of retinoids (i.e., compounds that bind to any members of the family of retinoid receptors), including, for example, tretinoin, retinol, esters of tretinoin and/or retinol and the like.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts.

The present invention encompasses biologically active analogs, homologs, derivatives, and modifications of the compounds of the invention. Methods for the preparation of such compounds are known in the art.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Liquid derivatives and natural extracts made directly from biological sources may be employed in the compositions of this invention in a concentration (w/w) from about 1 to about 99%. Fractions of natural extracts and protease inhibitors may have a different preferred rage, from about 0.01% to about 20% and, more preferably, from about 1% to about 10% of the composition. Of course, mixtures of the active agents of this invention may be combined and used together in the same formulation, or in serial applications of different formulations.

The composition of the invention may comprise a preservative from about 0.005% to 2.0% by total weight of the composition. The preservative is used to prevent spoilage in the case of an aqueous gel because of repeated patient use when it is exposed to contaminants in the environment from, for example, exposure to air or the patient's skin, including contact with the fingers used for applying a composition of the invention such as a therapeutic gel or cream. Examples of preservatives useful in accordance with the invention included but are not limited to those selected from the group consisting of benzyl alcohol, sorbic acid, parabens, imidurea, and combinations thereof. A particularly preferred preservative is a combination of about 0.5% to 2.0% benzyl alcohol and 0.05% to 0.5% sorbic acid.

The composition may include an antioxidant and a chelating agent which inhibit the degradation of the compound for use in the invention in the aqueous gel formulation. Preferred antioxidants for some compounds are BHT, BHA, alphatocopherol, and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are preferred antioxidant and chelating agent respectively for some compounds, other suitable and equivalent antioxidants and chelating agents may be substituted therefor as would be known to those skilled in the art.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Other components such as preservatives, antioxidants, surfactants, absorption enhancers, viscosity enhancers or film forming polymers, bulking agents, diluents, coloring agents, flavoring agents, pH modifiers, sweeteners or taste-masking agents may also be incorporated into the composition. Suitable coloring agents include red, black, and yellow iron oxides and FD&C dyes such as FD&C Blue No. 2, FD&C Red No. 40, and the like. Suitable flavoring agents include mint, raspberry, licorice, orange, lemon, grapefruit, caramel, vanilla, cherry grape flavors, combinations thereof, and the like. Suitable pH modifiers include citric acid, tartaric acid, phosphoric acid, hydrochloric acid, maleic acid, sodium hydroxide, and the like. Suitable sweeteners include aspartame, acesulfame K, thaumatic, and the like. Suitable taste-masking agents include sodium bicarbonate, ion-exchange resins, cyclodextrin inclusion compounds, adsorbates, and the like.

Absorption enhancers for use in accordance with the present invention include, for example, polysorbates, sorbitan esters, poloxamer block copolymers, PEG-35 castor oil, PEG-40 hydrogenated castor oil, caprylocaproyl macrogol-8 glycerides, PEG-8 caprylic/capric glycerides, sodium lauryl sulfate, dioctyl sulfosuccinate, polyethylene lauryl ether, ethoxydiglycol, propylene glycol mono-di-caprylate, glycerol monocaprylate, glyceryl fatty acids, oleic acid, linoleic acid, glyceryl caprylate/caprate, glyceryl monooleate, glyceryl monolaurate, caprylic/capric triglycerides, ethoxylated nonylphenols, PEG-(8-50) stearates, olive oil PEG-6 esters, triolein PEG-6 esters, lecithin, d-alpha tocopheryl polyethylene glycol 1000 succinate, polycarbonate, sodium glycocholate, sodium taurocholate, cyclodextrins, citric acid, sodium citrate, triacetin, combinations thereof, and the like. In certain preferred embodiments, the absorption enhancer is triacetin. In certain preferred embodiments wherein an absorption enhancer is included in the formulation, the absorption enhancer is included in an amount of from about 0.001% to about 10% by weight of the formulation, preferably in an amount of about 0.01% to about 5% by weight of the formulation.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, and birds including commercially relevant birds such as chickens, ducks, geese, and turkeys.

The pharmaceutical compositions of the invention can be administered in any suitable formulation, by any suitable means, and by any suitable route of administration. Formulations suitable for topical administration include, but are not limited to, liquid or semi-liquid preparations such as liniments, lotions, oil in water or water in oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Topical administration of compositions of the invention may include transdermal application. Transdermal application can be performed either passively or using iontophoresis or electroporation.

Compositions of the invention may be applied using transdermal patches. Transdermal patches are adhesive backed patches laced with an effective amount of compounds of the invention. The pressure-sensitive adhesive of the matrix will normally be a solution of polyacrylate, a silicone, or polyisobutylene (PIB). Such adhesives are well known in the transdermal art. See, for instance, the Handbook of Pressure Sensitive Adhesive Technology, 2nd Edition (1989) Van Nostrand, Reinhold.

Pressure sensitive solution polyacrylate adhesives for transdermal patches are made by copolymerizing one or more acrylate monomers ("acrylate" is intended to include both acrylates and methacrylates), one or more modifying monomers, and one or more functional group-containing monomers in an organic solvent. The acrylate monomers used to make these polymers are normally alkyl acrylates of 4-17 carbon atoms, with 2-ethylhexyl acrylate, butyl acrylate, and isooctyl acrylate being preferred. Modifying monomers are typically included to alter the Tg of the polymer. Such monomers as vinyl acetate, ethyl acrylate and methacrylate, and methyl methacrylate are useful for this purpose. The functional group-containing monomer provides sites for crosslinking. The functional groups of these monomers are preferably carboxyl, hydroxy or combinations thereof. Examples of monomers that provide such groups are acrylic acid, methacrylic acid and hydroxy-containing monomers such as hydroxyethyl acrylate. The polyacrylate adhesives are preferably crosslinked using a crosslinking agent to improve their physical properties, (e.g., creep and shear resistance). The crosslinking density should be low since high degrees of crosslinking may affect the adhesive properties of the copolymer adversely. Examples of crosslinking agents are disclosed in U.S. Pat. No. 5,393,529. Solution polyacrylate pressure sensitive adhesives are commercially available under tradenames such as GELVA™ and DURO-TAKT™ from 3M.

Polyisobutylene adhesives are mixtures of high molecular weight (HMW) PIB and low molecular weight (LMW) PIB. Such mixtures are described in the art, e.g., PCT/US91/02516. The molecular weight of the HMW PIB will usually be in the range of about 700,000 to 2,000,000 Da, whereas that of the LMW PIB will typically range between 35,000 to 60,000. The molecular weights referred to herein are weight average molecular weight. The weight ratio of HMW PIB to LMW PIB in the adhesive will normally range between 1:1 to 1:10. The PIB adhesive will also normally include a tackifier such as polybutene oil and high Tg, low molecular weight aliphatic resins such as the ESCOREZ™ resins available from Exxon Chemical. Polyisobutylene polymers are available commercially under the tradename VISTANEX™ from Exxon Chemical.

The silicone adhesives that may be used in forming the matrix are typically high molecular weight polydimethyl siloxanes or polydimethyldiphenyl siloxanes. Formulations of silicone adhesives that are useful in transdermal patches are described in U.S. Pat. Nos. 5,232,702, 4,906,169, and 4,951,622.

Dosage forms for topical or transdermal administration of a compound of this invention include liquids, ointments, pastes, creams, lotions, gels, powders, solutions, sprays, aerosols, inhalants or patches. The active component is admixed under sterile conditions with a pharmaceutically acceptable carrier and any needed preservatives or buffers as may be required. Ophthalmic formulation, ear drops, eye ointments, powders, and solutions are also contemplated as being within the scope of this invention. Transdermal patches have the added advantage of providing controlled delivery of a compound to the body. Such dosage forms can be made by dissolving or dispensing the compound(s) in the proper medium. Absorption enhancers can also be used to increase the flux of the compound across the skin. The rate can be controlled by either providing a rate controlling membrane or by dispersing the compound in a polymer matrix or gel.

The ointments, pastes, creams, and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Topical administration may also be performed using iontophoresis devices. Such delivery systems eliminate needles entirely, and rely upon chemical mediators or external driving forces such as iontophoretic currents or thermal poration or sonophoresis to breach the stratum corneum, the outermost layer of the skin, and deliver substances through the surface of the skin. The process of iontophoresis has found commercial use in the delivery of ionically charged therapeutic agent molecules such as pilocarpine, lidocaine, and dexamethasone. In this delivery method, ions bearing a positive charge are driven across the skin at the site of an electrolytic electrical system anode while ions bearing a negative charge are driven across the skin at the site of an electrolytic system cathode.

The present invention provides a system for the direct application of compounds of the invention, including additional therapeutic agents such as anesthetic agents, by iontophoresis for the treatment of decreased blood flow and concurrent pain associated with injuries, diseases, and disorders. While many compounds may be useful with the invention, as will be discussed below, it is particularly useful for the delivery of anesthetic agents such as lidocaine, bupivicaine, ropivicaine, and mepivicaine to damaged skin.

In one embodiment, the methods of the invention provide a patch device with a donor or delivery chamber that is designed to be applied directly over an injury, incision, or wound site and utilizes an electric field to stimulate delivery of the active compound or additional therapeutic agents(s). The patch is sterilized so that risk of infection is minimal. Additionally, the system delivers medication in a constant manner over an extended period of time. Generally, such time periods are at least 30 minutes and may extend to as many as 96 hours.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally, the propellant may constitute about 50% to about 99.9% (w/w) of the composition, and the active ingredient may constitute about 0.1% to about 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to about 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as about 0.1% (w/w) and as much as about 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, comprise about 0.1% to about 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and may further comprise one or more of the additional ingredients described herein. Additionally, the formulation taken orally can be prepared as a pharmaceutical composition, including, but not limited to, a paste, a gel, a toothpaste, a mouthwash, a solution, an oral rinse, a suspension, an ointment, a cream, and a coating.

A pharmaceutical composition of the invention may be prepared, packaged, or sold in a formulation suitable for ophthalmic administration. Such formulations may, for example, be in the form of eye drops including, for example, a 0.1% to 1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

A pharmaceutical composition of the invention may be prepared, packaged, or sold in a formulation suitable for intramucosal administration. The present invention provides for intramucosal administration of compounds to allow passage or absorption of the compounds across mucosa. Such type of administration is useful for absorption orally (gingival, sublingual, buccal, etc.), rectally, vaginally, pulmonary, nasally, etc.

In some aspects, sublingual administration has an advantage for active ingredients, as well as additional therapeutic agents, which in some cases, when given orally, are subject to a substantial first pass metabolism and enzymatic degradation through the liver, resulting in rapid metabolization and a loss of therapeutic activity related to the activity of the liver enzymes that convert the molecule into inactive metabolites, or the activity of which is decreased because of this bioconversion.

In some cases, a sublingual route of administration is capable of producing a rapid onset of action due to the considerable permeability and vascularization of the buccal mucosa. Moreover, sublingual administration can also allow the administration of active ingredients which are not normally absorbed at the level of the stomach mucosa or digestive mucosa after oral administration, or alternatively which are partially or completely degraded in acidic medium after ingestion of, for example, a tablet.

The compounds of the invention can be prepared in a formulation or pharmaceutical composition appropriate for administration that allows or enhances absorption across mucosa. Mucosal absorption enhancers include, but are not limited to, a bile salt, fatty acid, surfactant, or alcohol. In specific embodiments, the permeation enhancer can be sodium cholate, sodium dodecyl sulphate, sodium deoxycholate, taurodeoxycholate, sodium glycocholate, dimethylsulfoxide, or ethanol. In a further embodiment, a compound of the invention can be formulated with a mucosal penetration enhancer to facilitate delivery of the compound. The formulation can also be prepared with pH optimized for solubility, drug stability, and absorption through mucosa such as nasal mucosa, oral mucosa, vaginal mucosa, respiratory, and intestinal mucosa.

To further enhance mucosal delivery of pharmaceutical agents within the invention, formulations comprising the active agent may also contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10000 and preferably not more than 3000. Exemplary hydrophilic low molecular weight compounds include polyol compounds, such as oligo-, di- and monosaccharides such as sucrose, mannitol, lactose, L-arabinose, D-erythrose, D-ribose, D-xylose, D-mannose, D-galactose, lactulose, cellobiose, gentibiose, glycerin, and polyethylene glycol. Other examples of hydrophilic low molecular weight compounds useful as carriers within the invention include N-methylpyrrolidone, and alcohols (e.g., oligovinyl alcohol, ethanol, ethylene glycol, propylene glycol, etc.). These hydrophilic low molecular weight compounds can be used alone or in combination with one another or with other active or inactive components of the intranasal formulation.

When a controlled-release pharmaceutical preparation of the present invention further contains a hydrophilic base, many options are available for inclusion. Hydrophilic polymers such as a polyethylene glycol and polyvinyl pyrrolidone, sugar alcohols such as D-sorbitol and xylitol, saccharides such as sucrose, maltose, lactulose, D-fructose, dextran, and glucose, surfactants such as polyoxyethylene-hydrogenated castor oil, polyoxyethylene polyoxypropylene glycol, and polyoxyethylene sorbitan higher fatty acid esters, salts such as sodium chloride and magnesium chloride, organic acids such as citric acid and tartaric acid, amino acids such as glycine, beta-alanine, and lysine hydrochloride, and aminosaccharides such as meglumine are given as examples of the hydrophilic base. Polyethylene glycol, sucrose, and polyvinyl pyrrolidone are preferred and polyethylene glycol are further preferred. One or a combination of two or more hydrophilic bases can be used in the present invention.

The present invention contemplates pulmonary, nasal, or oral administration through an inhaler. In one embodiment, delivery from an inhaler can be a metered dose.

An inhaler is a device for patient self-administration of at least one compound of the invention comprising a spray inhaler (e.g., a nasal, oral, or pulmonary spray inhaler) containing an aerosol spray formulation of at least one compound of the invention and a pharmaceutically acceptable dispersant. In one aspect, the device is metered to disperse an amount of the aerosol formulation by forming a spray that contains a dose of at least one compound of the invention effective to treat a disease or disorder encompassed by the invention. The dispersant may be a surfactant, such as, but not limited to, polyoxyethylene fatty acid esters, polyoxyethylene fatty acid alcohols, and polyoxyethylene sorbitan fatty acid esters. Phospholipid-based surfactants also may be used.

In other embodiments, the aerosol formulation is provided as a dry powder aerosol formulation in which a compound of the invention is present as a finely divided powder. The dry powder formulation can further comprise a bulking agent, such as, but not limited to, lactose, sorbitol, sucrose, and mannitol.

In another specific embodiment, the aerosol formulation is a liquid aerosol formulation further comprising a pharmaceutically acceptable diluent, such as, but not limited to, sterile water, saline, buffered saline and dextrose solution.

In further embodiments, the aerosol formulation further comprises at least one additional compound of the invention in a concentration such that the metered amount of the aerosol formulation dispersed by the device contains a dose of the additional compound in a metered amount that is effective to ameliorate the symptoms of disease or disorder disclosed herein when used in combination with at least a first or second compound of the invention.

Compounds of the invention will be prepared in a formulation or pharmaceutical composition appropriate for nasal administration. In a further embodiment, the compounds of the invention can be formulated with a mucosal penetration enhancer to facilitate delivery of the drug. The formulation can also be prepared with pH optimized for solubility, drug stability, absorption through nasal mucosa, and other considerations.

Capsules, blisters, and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

For administration by inhalation, the compounds for use according to the methods of the invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount. Capsules and cartridges of e.g., gelatin for use in an inhaler or insufflator may be formulated containing a powder mix of the drugs and a suitable powder base such as lactose or starch.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically, dosages of the compounds of the invention which may be administered to an animal, preferably a human, range in amount from about 1.0 µg to about 100 g per kilogram of body weight of the animal. The precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compounds may be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

Biosensors, Chemical Sensors, and Data Display

Compositions of the invention comprising metal nanoparticles are also useful for other methods, including, for example, as sensors and for data display. In one embodiment, the method of present invention employs nanosize particles for detection of molecular structures of interest. It is appreciated that the method of present invention is not bound to any particular assumption or theory of the mechanism of interaction of the chemical groups present on the substrate surface and said nano-particles. The method of present invention can be practiced by many different ways. Various other embodiments and variations to the preferred embodiments will be apparent to those skilled in the art and may be made without departing from the spirit and scope of the following claims.

Nucleic acid hybridization has become an increasingly important technology for DNA analysis and gene expression studies. For example, DNA and RNA hybridization techniques are very useful for detecting, identifying, fingerprinting, and mapping molecular structures. Recently developed combinatorial DNA chips, which rely on the specific hybridization of target and probe DNA on a solid surface, are also encompassed by the present invention. Proteomics has also introduced a very valuable complimentary approach to study the biological functions of a cell. Proteomics involves the qualitative and quantitative measurement of gene activity by detecting and quantifying expressions at the protein level, rather than at the messenger RNA level. Multianalyte assays, also known in the art as "protein chips", involve the use of multiple antibodies and are directed towards assaying for multiple analytes. The approach enables rapid, simultaneous processing of thousands of proteins employing automation and miniaturization strategy introduced by DNA microarrays.

Currently, the most common approach to detect DNA bound to a microarray is to label it with a reporter molecule that identifies DNA presence. The reporter molecules emits detectable light when excited by an external light source. Light emitted by a reporter molecule has a characteristic wavelength, which is different from the wavelength of the excitation light, and therefore a detector such as a Charge-Coupled Device (CCD) or a confocal microscope can selectively detect a reporter's emission. Although the use of optical detection methods increases the throughput of the sequencing experiments, the disadvantages are serious. Incorporation of a fluorescent label into a nucleic acid sequence increases the complexity and cost of the entire process. Although the chemistry is commonplace, it necessitates additional steps and reagents for fluorescent labeling, and can be accomplished only with specialized expensive equipment for detection of weak fluorescent signals.

Autoradiography is another common technique for the detection of molecular structures. For DNA sequence analysis applications, oligonucleotide fragments are end labeled, for example, with $^{32}P$ or $^{35}S$. These end labeled fragments are then exposed to X-ray film for a specified amount of time. The amount of film exposure is determined by densitometry and is directly related to the amount of radioactivity of the labeled fragments adjacent to a region of film.

The use of any radioactive label has several disadvantages. First, the use of radioactive isotopes increases the risk of workers acquiring mutation-related diseases. As such, precautions must be implemented when using radioactive markers or labels. Second, the need of an additional processing step and the use of additional chemical reagents and short-lived radioisotopes increases the cost and complexity of this detection technique.

A method of using metal nanoparticles, as an alternative detection agent for detection of nucleic acids on microarrays without using specialized expensive equipment for detection is taught in U.S. Pat. Nos. 6,495,324 and 6,682,895. The nucleotides having sequence complimentary to the target nucleic acid first are attached to the surface of gold nano-particles (nanoparticle-oligonucleotide conjugates). The gold nano-particles conjugates that hybridized with target molecules hybridized to the probes on microarray surface. In this method the hybridization of gold conjugates marks array spots where target molecules are located. However, the method required a large number of sequence-specific oligonucleotides for manufacturing nano-particle conjugates, which seen as the significant disadvantage of the oligonucleotide-conjugate method. In addition, oligonucleotides-gold conjugates are often unstable under the typical hybridization conditions, which further complicates the use of gold-oligonucleotides conjugates (see Li et al., "Multiple thiol-anchor capped DNA-gold nanoparticle conjugates", Nuc. Acids Res., 30(7), 1558-1562 (2202)).

Yguerabide et al., U.S. Pat. No. 6,586,193, describes a method of using light scattering for sensitive detection of target biopolymers. In this method another type of metal-conjugate particles described, which conjugates provides specific binding component to bind target molecules through hapten pairs, such as biotin/streptavidin or digoxigenin/anti-digoxigenin and the similar binding systems. In some embodiments of the method the particles are coated with, for instance, streptavidin wherein biotin is incorporated into the structure of target molecules during the steps of analyte preparation. Yet, the modification of target molecules by incorporating labeling group(s) (e.g., biotin and the similar) for detection often introduces bias, reduces accuracy and increases the cost and complexity of microarray analysis.

Remade et al., US App. No. 2003/0096321, describes a method for identification of a labeled target compound on a surface of solid support. In one embodiment, the use of non-modified target molecules is described by employing a sandwich type assay, in which the target is hybridized with an additional labeled nucleotide sequence, which labeled nucleotide allows attachment of gold-conjugates to the target compound. Yet, once again, the method requires the use of a large number of labeled sequence-specific oligonucleotides, which makes the method unpractical. The modification of this approach for reducing the number of various labeled sequence-specific oligonucleotides, in which universal binding sequences such as polyT and polyA nucleotides are used, has a limited utility and cannot be used for analysis of partially degraded mRNA, which lost partially or completely the polyA tail or for analysis of microbial mRNA, which do not have polyA tail.

While a large number of detection methods for use with nucleic acids and protein arrays have been described in patents and in the scientific literature, virtually all methods set forth in prior art contain one or more inherent weaknesses. Some lack the sensitivity necessary to accomplish certain tasks. Other methods lack the recognition specificity due to imposing non-optimal conditions for forming probe-target duplexes. Still others are expensive and difficult to implement due to complexity of sample preparation and often have drawbacks due to bias introduced by labeling groups incorporated into the structure of target molecules.

Thus, there is a need for an improved method for visualization of molecular structures, which method is quantitative, sensitive, and simple to implement.

For quantification of the hybridized target molecules, the surface of the solid support (i.e., microarray) covered by nanoparticles can be analyzed and density of the bound nanoparticles can be measured using conventional optical techniques and a suitable image-capturing apparatus. A suitable image-capturing apparatus can include any device of plurality of devices capable of acquiring absorbance on the surface and reflectance from the surface of interest, and most preferably, includes flatbed scanners. The resolution of the image-capturing device must be sufficient to identify optical response from individual test sites on the surface of the substrate. Most preferably, the image-capturing device must be able to digitize the captured image and transfer the image to a computer for storage and further analysis. It is appreciated that images of the same area of the substrate can be captured multiple times for averaging, reducing noise, color manipulations, filtering and performing other image-processing operations known to one skilled in the art. Specialized software can be implemented for obtaining quantitative characteristics of the optical response from each individual test site on the substrate. These quantitative parameters can be used to quantify the distribution of nano-particles bound to the substrate and accordingly to measure the quantity of molecular structure of interest in corresponded site(s) of the substrate.

The present invention may be embodied in other specific forms without departing from the spirit or essential attributes thereof. This invention encompasses all combinations of the different aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

The examples provided throughout his application are non-inclusive unless otherwise stated. They include but are not limited to the recited examples.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1

A. Development of Nanostructured Metal Surfaces Containing Silver Nanoparticles

Surface Modification of Titanium Metal by Surface Etching Followed by Silver Nanoparticle Formation Titanium thin films were procured from Good Fellow Inc. The metal film was cut into 1×1 cm. square samples for surface modification. The samples were washed with acetone, 1% triton followed by mild sonication in distilled water.

The morphology of the metal surfaces, both before and after surface modifications, was evaluated using secondary electron imaging (SEI) in a JEOL 6700F scanning electron microscope (SEM). The elemental composition of the modified surface was evaluated using energy dispersive spectroscopy (PGT Light Element Detector running Spirit software).

FIG. 1 shows images of scanning electron micrographs of unmodified titanium sample indicating the morphology. FIG. 2 shows the elemental composition of the unmodified metal film indicating that the surface is composed solely of titanium metal.

Figure 3B:
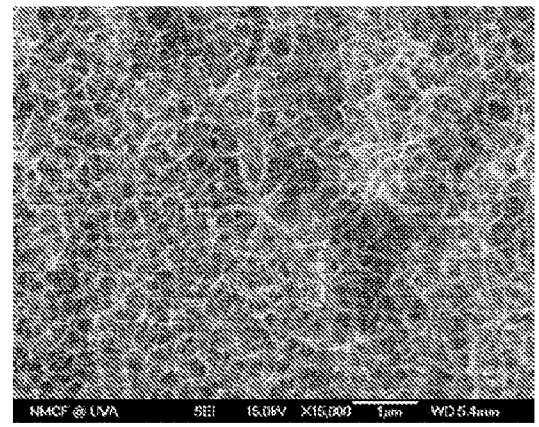
Figure 4A:
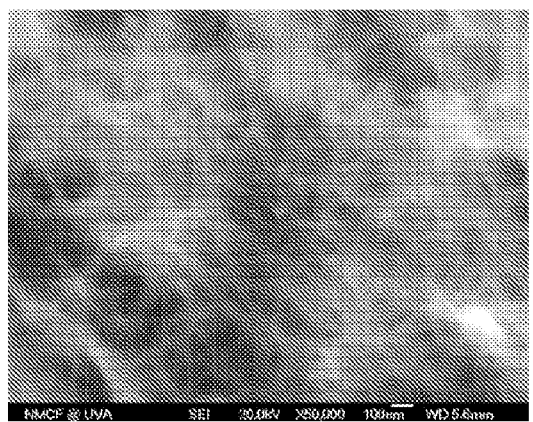
FIG. 4. Surface morphology of etched titanium thin films at two different higher magnifications (4A—×50,000; 4B—×100,000)
Figure 4B:
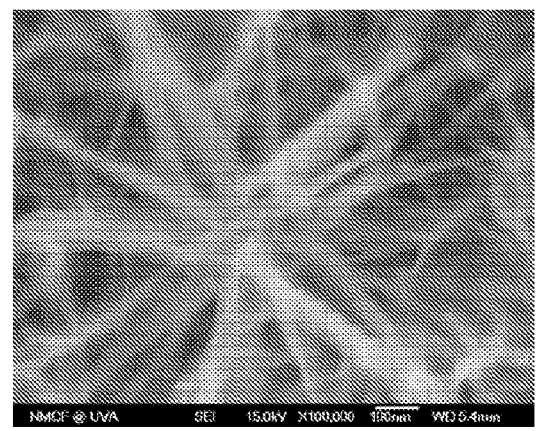

Surface Etching of Titanium Thin Films:

The washed samples were incubated in 5 M sodium hydroxide solution at 40° C. for 24 h. After the incubation time the samples were washed with water twice and dried under vacuum. FIGS. 3 and 4 represent scanning electron micrographs of base etched titanium sample showing the morphology. Under the present etching conditions, the surface of the metal showed a uniform nanofibrous structure. The gross morphology of the structure was found to be highly reproducible. The fibrous structure on the surface was found to have an average diameter of less than ~100 nm.

Figure 5:
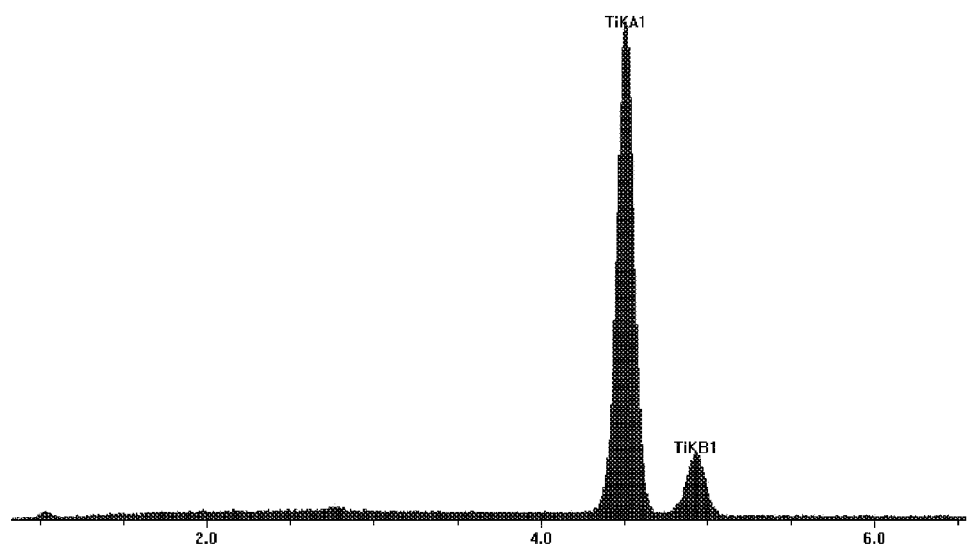
FIG. 5. Surface elemental composition of titanium indicating the presence of only titanium atom.

FIG. 5 shows the EDS spectra of surface etched titanium films. The surface mainly shows the presence of titanium metal on the surface. The absence of sodium peak on the surface can be attributed to washing the surface with water.

Figure 6A:
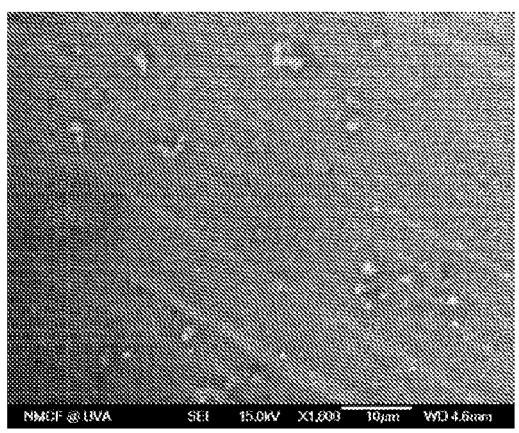
FIG. 6. Surface morphology of silver nitrated treated etched titanium films (6A—×1,600; 6B—×5,500).
Figure 6B:
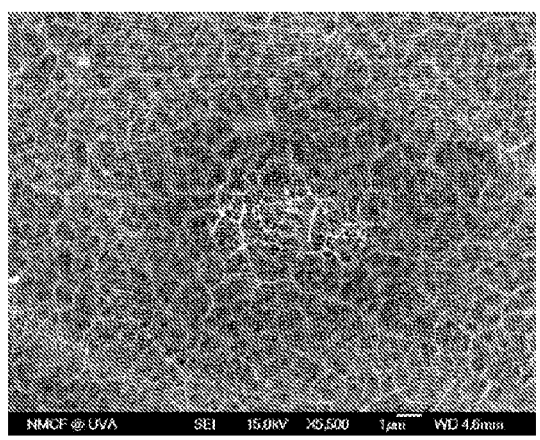
Figure 7A:
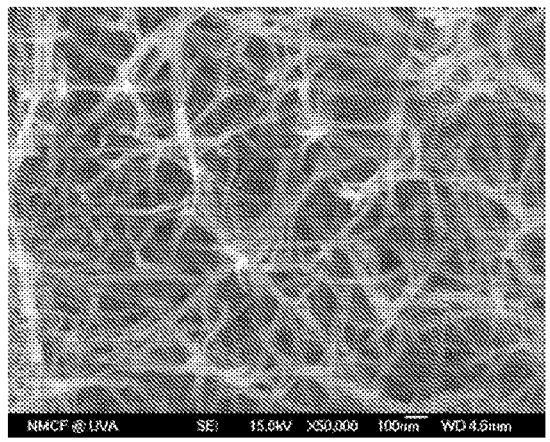
FIGS. 7a-7c, depicts surface morphology of silver nitrated treated etched titanium films at different magnifications (7a—×50,000; 7b—×300,000; 7c—×100,000).
Figure 7B:
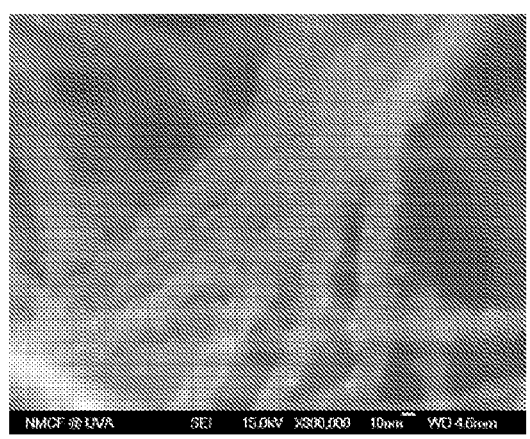
Figure 7C:
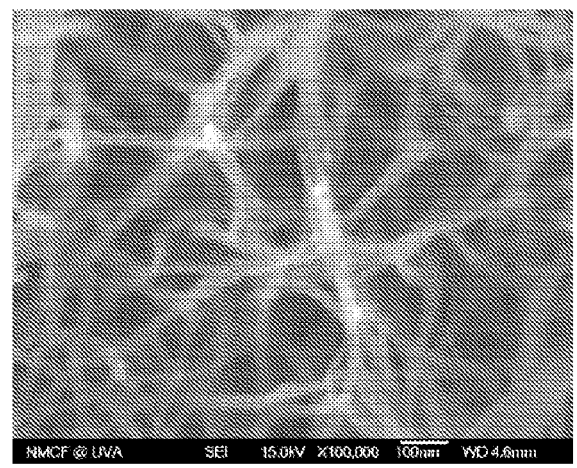
Figure 8:
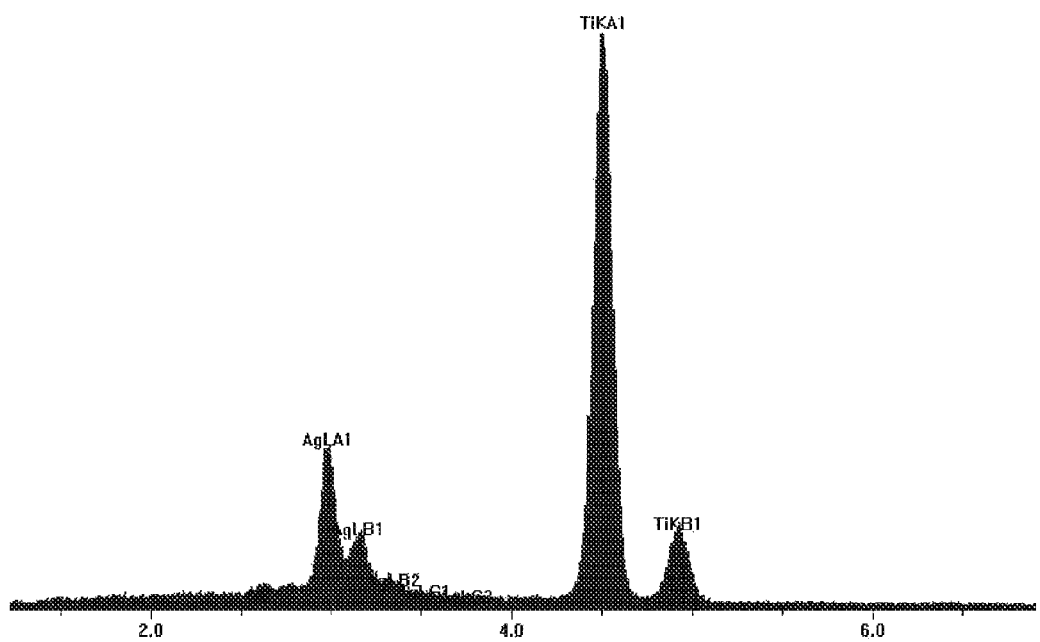
FIG. 8. Surface elemental composition of silver nitrated treated etched titanium films.
Figure 10:
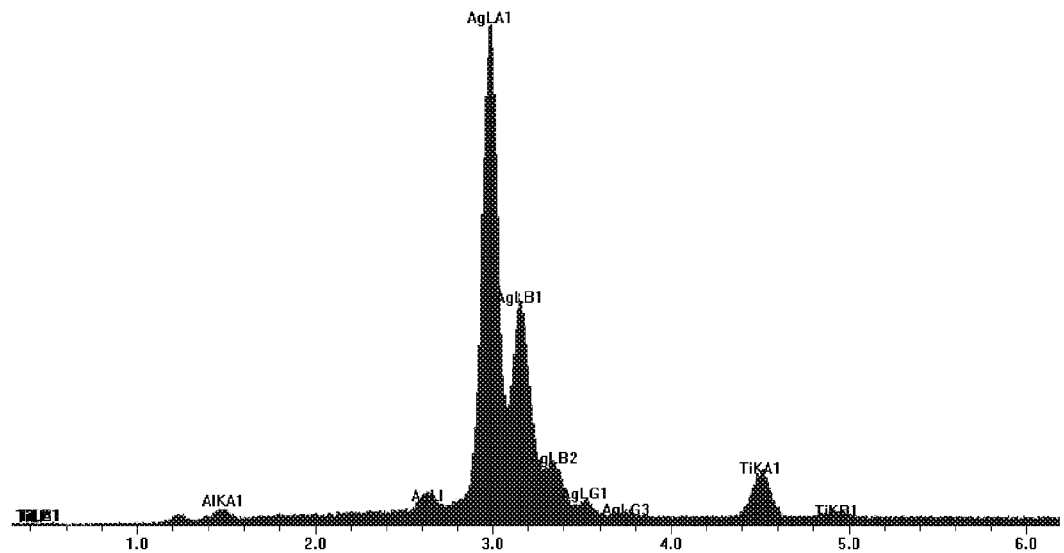
FIG. 10 represents EDS spectra of the nanoparticles on the surface indicating the composition as silver.
Figure 11:
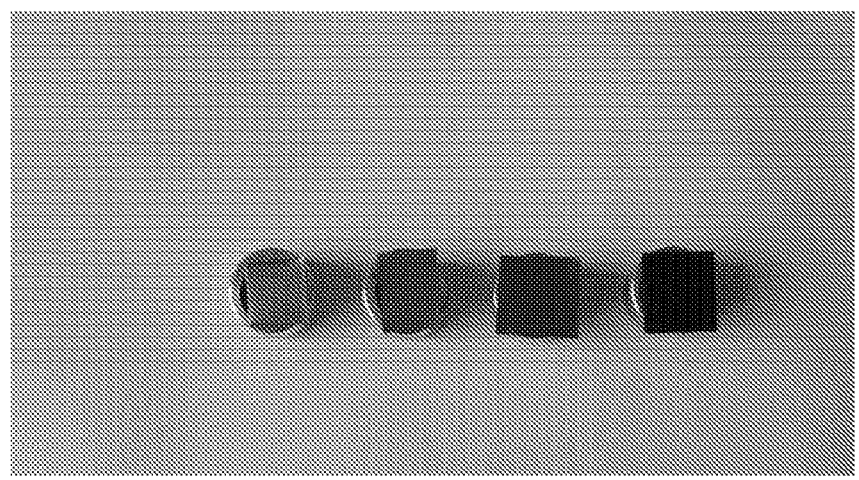
FIG. 11, comprising

Surface Functionalization of Etched Titanium Films Using Silver Nitrate Solution The etched titanium films were incubated in 50 mM silver nitrate solution in water at 40° C. for 24 h. After the incubation time the samples were washed with water twice and dried under vacuum. FIGS. 6 and 7 represent scanning electron micrographs showing the morphology of base etched titanium films incubated in silver nitrate solution. Again the gross morphology of the structure was found to be highly reproducible (n=3). FIGS. 7 and 8 clearly demonstrate the presence of silver on the surface of base etched titanium surfaces. However, contrary to what was expected, high magnified image (FIG. 7b) clearly shows the formation of few nanoparticles (~10 nm) on the surface of the metal even though no reducing agents have been used. FIGS. 9 and 10 shows the surface of alkali etched titanium surface treated with silver ions after reduction using sodium borohydride. As shown in the figure, reduction of silver ions significantly increased. The size of the silver particles were found to range from ~5-10 nm. The formation of silver nanoparticles was further confirmed by EDS spectra (FIG. 10). The nanofibrous structure present on the surface due to titanium has been found to have very small diameter in the range of 10-20 nm. This unique structure results in the formation of unique color change to the metal. FIG. 11 shows the photographs of surface modified and unmodified titanium films. The formation of silver nanoparticles changed the color of the film to brown-blue color with a metallic luster. Further studies showed significant reduction of bacteria on the surface comprising metallic nanoparticles and showed the use for the metal substrates for growing mammalian cells (see Example 4 and FIG. 32).

B. Development of Nanostructured Polymeric Surfaces Containing Silver Nanoparticles For polymeric substrates, we have developed an unique surface coating technique to modify the surfaces of polymeric biomaterials and devices with silver nanoparticles. The process is based on the photochemistry of azides. Briefly polymeric substrates either carboxylated, aminated or hydroxylated (any reactive functional groups) polymers can be functionalized with aromatic or aliphatic azides to make them photoactive. The photoactive polymers can be permanently coated on any substrates by photoirradiation. In the case of aromatic azides, the absorption occurs in the range of ~275 nm and therefore irradiation of the coated surface with UV radiation result in immobilization of the polymer on the surface due to an azide insertion reaction.

Figure 20:
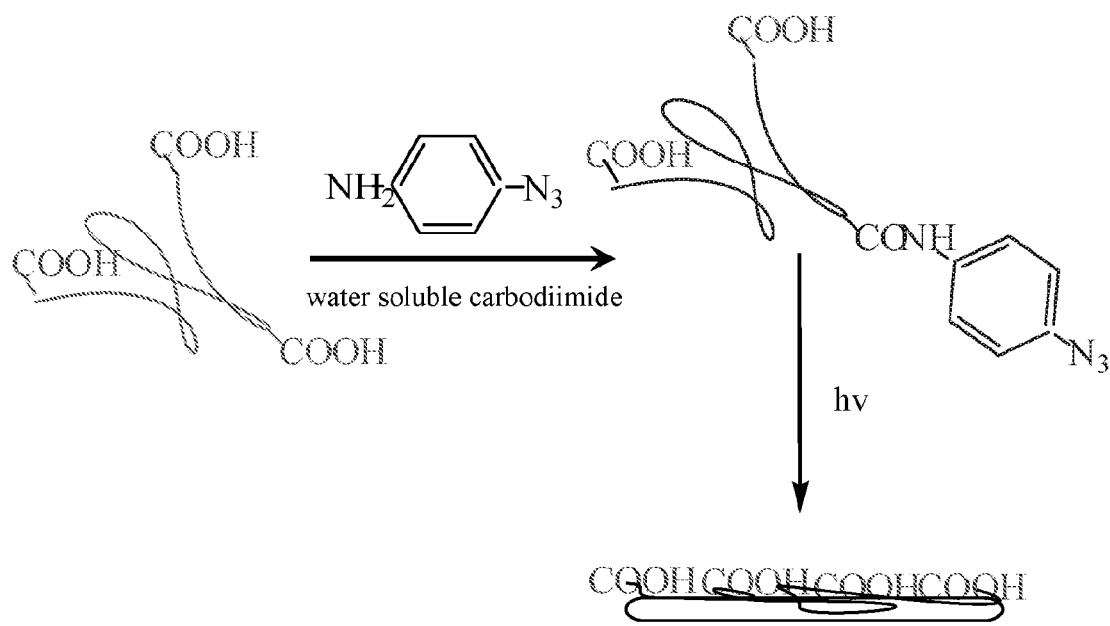
FIG. 20. Scheme showing the preparation and photo-immobilization of azidated polymers.

A typical procedure for the modification of polymeric substrates with azide group is as follows:

Preparation of Photoactive Carboxylated Polymers:

The carboxylated polymers [poly(acrylic acid), alginica acid, heparin and chondroitin sulfate) were treated with 4-azidoaniline hydrochloride in the presence of water soluble carbodiimide and N-hydroxysuccinimide in distilled water. N-hydroxysuccinimide is commonly used as an activating reagent for carboxylic acids. The pH of the solution was adjusted to ~4 using sodium hydroxide solution and the resulting solution was stirred overnight at 4° C. in dark. The ratios of the reagents was varied to get a substitution of 10, 30, and 50% of carboxyl groups with azidoaniline groups. The chemically modified polymer was purified by dialysis against water at 4° C. in dark for 48 h. The resulting purified polymer solution was lyophilized for 72 h and the dry polymer powder was kept at −20° C. (FIG. 20). FIG. 12 shows the UV spectra of azidated polymer showing strong absorbance in the 275-280 nm due to the aromatic azide groups.

Surface Immobilization of Azidated Polymers

The azidated polymers was dissolved in double distilled water and coated onto polymeric substrates. Commercially available polystyrene cover slips were commonly used, however feasibility to coat on other polymers have also been demonstrated. Different polymer concentrations were used for coating including 10 mg/ml, 5.0 mg/ml, 1.0 mg/ml, and 0.05 mg/ml. The coating was allowed to dry over night in the dark. The coated surface was then irradiated with UV radiation at a wave length of 275 nm for 2-3 minutes for azidated polymer immobilization on the substrate (FIG. 20). The coated substrate was then sonicated in water for 1-2 min to wash off the unattached polymer. The coated substrate was then dried under vacuum.

Incorporation of Silver Ions on the Surface by Ion Exchange Method

The photomodified polymeric substrates were incubated in silver nitrate solution (10-50 μM) at 37° C. for various periods of time (5 h-24 h). The silver ion complexed surfaces were washed with distilled water and dried under vacuum. The reduction of silver ions to silver metal can be performed using various reducing agents. This includes, for example, 5-10 μM solution of sodium borohydride in water, solution of dextrose in water. In other cases, a basic ammoniacal silver nitrate solution can be used for ion exchange method for direct reduction of ions to metal. The modified polymeric substrates shows unique colors depending on the method of reduction and will be extensively washed with water and dried under vacuum. FIG. 13 shows silver nanoparticles formed on polystyrene surface coated with silver nanoparticles. The coated surfaces were incubated in silver nanoparticles for 24 h before reduction. The white spots have been identified as silver nanoparticles uniformly distributed in the surface of the polymer coating. FIG. 14 demonstrates the different sizes and distribution of silver nanoparticles formed on azidated alginic acid on polystyrene cover slips after ion exchanging with silver followed by reduction.

Figure 14A:
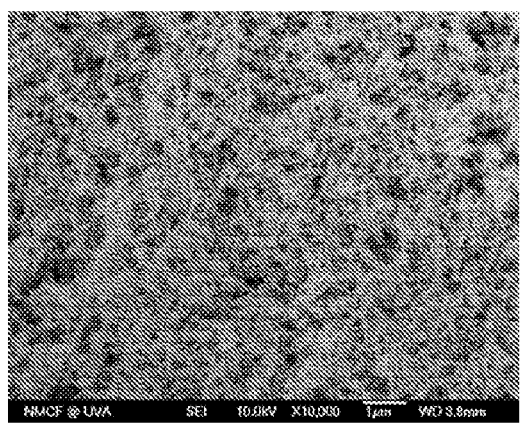
FIGS. 14A-E, illustrates the different sizes and size distribution of silver nanoparticles formed on azidated alginic acid on polystyrene cover slips after ion exchanging with silver followed by reduction.
Figure 14B:
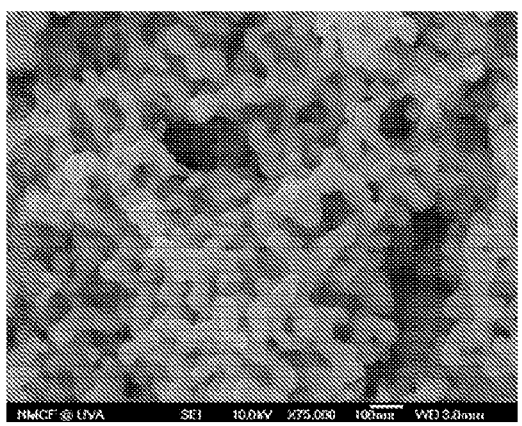
Figure 14C:
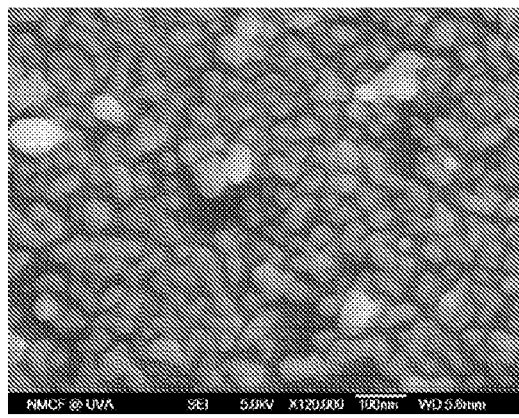
Figure 14D:
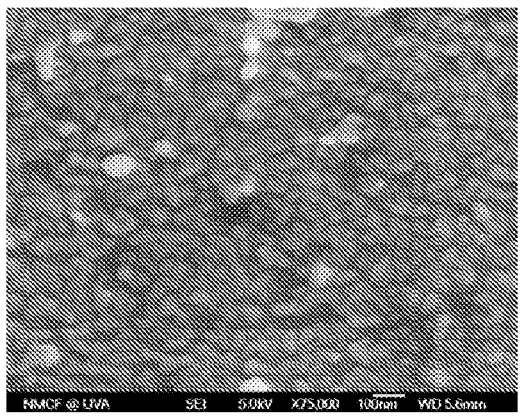
Figure 14E:
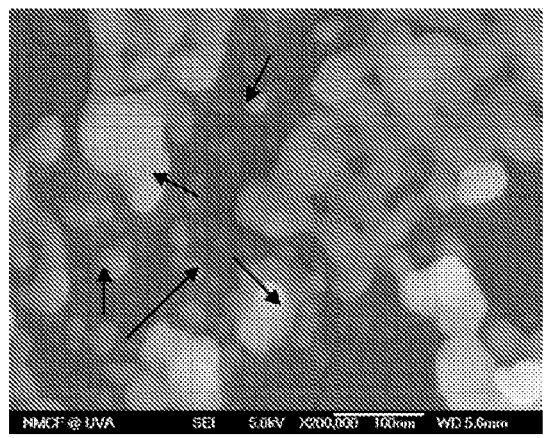

Spot EDS spectra has identified the elemental composition of the surface (FIG. 14E). The arrows (and regions with similar color) indicates silver on the surface. The dark background indicated by the arrow on the far right indicates regions rich in carbon and oxygen and is therefore presumably the alginic acid substrate.

C. Preparation of Silver Nanoparticles Using Ammoniacal Polysaccharides

Figure 17A:
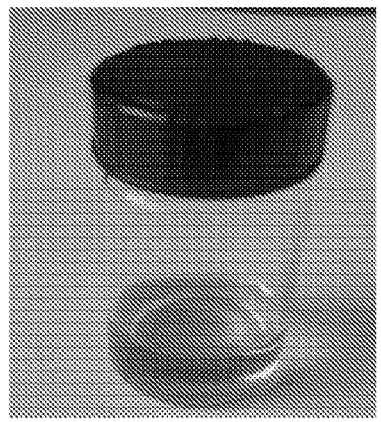
FIG. 17. Formation of silver nanoparticles on azidated heparin sulfate coated on polystyrene substrate, after silver ion exchange and reduction using sodium borohydride. 17a—Silver nanoparticles formed in solution w/o adding NaBH4; 17b—UV absorption spectra characteristic of Ag nanoparticle.
Figure 17B:
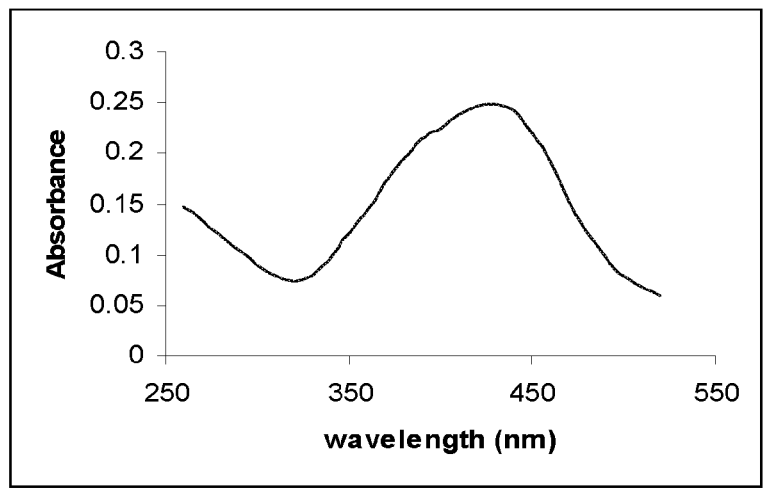

During this process, we demonstrated the feasibility of developing silver nanoparticles by treating silver nitrate solution in the presence of sodium hydroxide and ammonium hydroxide in a polysaccharide solution. Feasibility of developing silver nanoparticles without using reducing agents: Silver nanoparticles have been shown to be formed in the presence of reducing sugars at above neutral pHs. We have found that ammoniacal solution of azidated polymers such as heparin sulfate at appropriate concentrations can directly form silver nanoparticles without the use of strong reducing agents such as sodium borohydride. FIGS. 17a & b show the nanoparticles formed in solution and its UV absorption spectra. This will be further investigated in the proposed study as a single step Green Synthetic route for making nanoparticles on substrates.

We are currently investigating this reduction method as the novel environmentally friendly reducing process compared to using strong reducing agents such as sodium borohydride in forming the silver nanoparticles. We are also currently investigating polymeric aldehyde as a substrate for direct reduction of metals to form stable nanoparticles. We are using natural polymeric aldehydes (which are prepared by the sodiumperiodate reduction of polysaccharides) as a template for the direct reduction of nanoparticles based on a reaction similar to Tollen's reaction [13]. The same azide chemistry described earlier can be used to immobilize these aldehyde substituted polymers on the surface for various applications. Feasibility of developing silver nanoparticle coatings on nanofibers: Photografting process can also be used to form nanoparticles on a variety of structures. FIGS. 18a and 18b shows nanoparticles formed on polymeric nanofiber matrices using two different concentrations of the azidated polymer coating solutions.

Feasibility of Patterning Surfaces with Metal Particles

Figure 21:
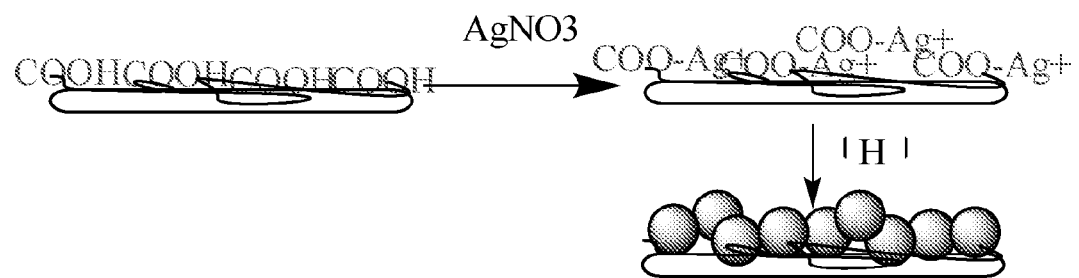
FIG. 21. Scheme showing the formation of silver nanoparticles on polymeric substrates.

We have also demonstrated the feasibility of patterning metal nanoparticles on the surface by using azidated polymers. FIG. 19A shows poly(acrylic azide) coated and shined with UV light through a photomask. The yellow region (appears as a lighter shade in a black and white photograph) shows polyacrylic acid grafted on polystyrene surface. FIG. 19B shows silver nanoparticles formed on the polyacrylic acid patterns on polystyrene. FIG. 20 schematically illustrates the preparation and photo-immobilization of azidated polymers. FIG. 21 schematically illustrates the formation of silver nanoparticles on polymeric substrates.

Example 2

Preparation of PluroGel-Silver Particle Composites

Procedure 1: 30 mg of Silver in 9.5 mL of Neat PluroGel.
2 mL of PluroGel was aliquoted and stirred using a magnetic stirrer at 4° C. in an icebath. 0.01 gm of silver nitrate powder was then added to PluroGel. The color of the solution instantly turned to yellow. The solution was stirred for another 2-5 minutes to form the silver nanoparticle-PluroGel composite mixture. The solution showed phase transition (liquid to solid) when heated to 37° C. in a water bath.

Procedure 2: 30 mg of Silver Solution in 9.5 mL of Neat PluroGel 2 mL of PluroGel was aliquoted and stirred using a magnetic stirrer at 4° C. in an icebath. 100 µL of 10% solution of silver nitrate in water was then added to PluroGel. The color of the solution instantly turned to yellow. The solution was stirred for another 2-5 minutes to form the silver particle-PluroGel composite mixture. The solution showed phase transition (liquid to solid) when heated to 37° C. in a water bath.

Procedure 3: 30 mg of Silver Solution in 9.5 mL of Neat PluroGel 2 mL of PluroGel was aliquoted and stirred using a magnetic stirrer at 4° C. in an icebath. 200 µL of 5% solution of silver nitrate in water was then added to PluroGel. The color of the solution instantly turned to yellow. The solution was stirred for another 2-5 minutes to form the silver particle-PluroGel composite mixture. The solution showed phase transition (liquid to solid) when heated to 37° C. in a water bath.

Procedure 4: 30 mg of Silver Solution in 9.5 mL of Neat PluroGel 2 mL of PluroGel was aliquoted and stirred using a magnetic stirrer at 4° C. in an icebath. 400 µL of 2.5% solution of silver nitrate in water was then added to PluroGel. The color of the solution instantly turned to yellow. The solution was stirred for another 2-5 minutes to form the silver particle-PluroGel composite mixture. The solution did not show phase transition (liquid to solid) when heated to 37° C. in a water bath.

For 2 mL of PluroGel, addition of ~200 µL of silver nitrate solution retained the solution's temperature induced transition.

The procedure was also performed using a diluted formulation of PluroGel which is less viscous at room temperature. Using the diluted formulation, the above procedures were performed at room temperature rather than 4° C.

The present invention further encompasses methods for preparing and using surface active polymers, including Pluro-Gel and variations thereof as described in International Application No. PCT/US2008/066094 (Katz and Rodeheaver), filed Jun. 6, 2008, the contents of which are hereby incorporated in their entirety herein.

Figure 22:
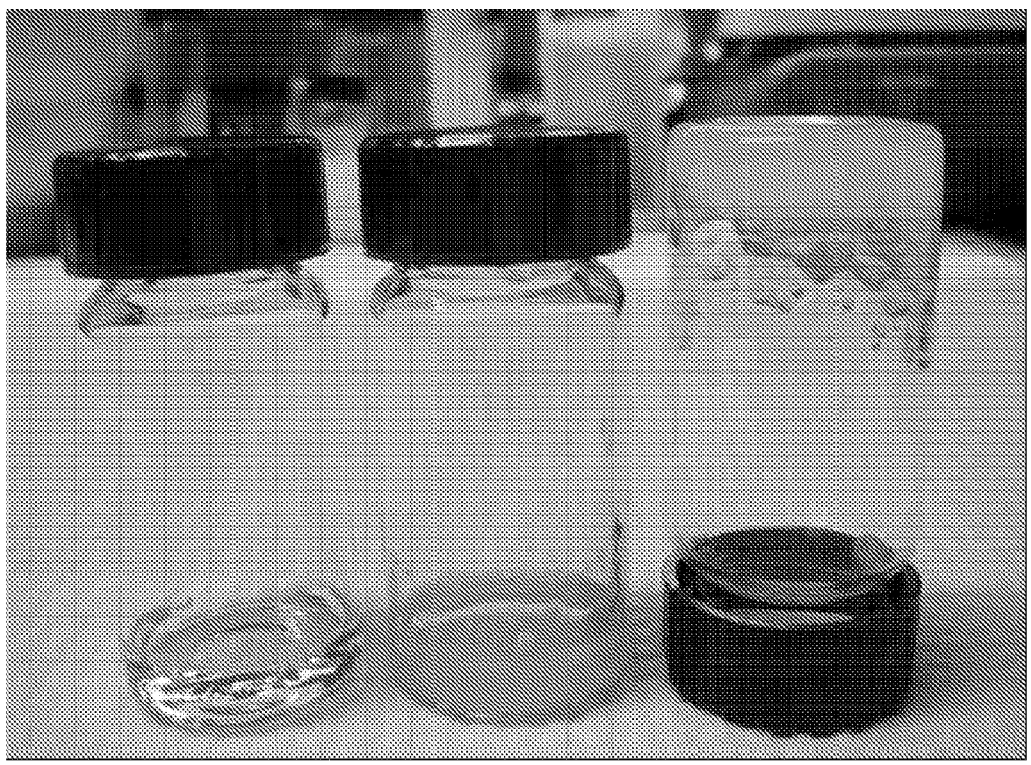
FIG. 22 represents a photographic image illustrating the phase transition of PluroGel in the presence of silver nanoparticles formed using Procedure 1, as described in Example 2. Three vials, labeled A, B, and C are depicted. The photograph of FIG. 22 also demonstrates visually the differences between PluroGel at 4° C.
Figure 23:
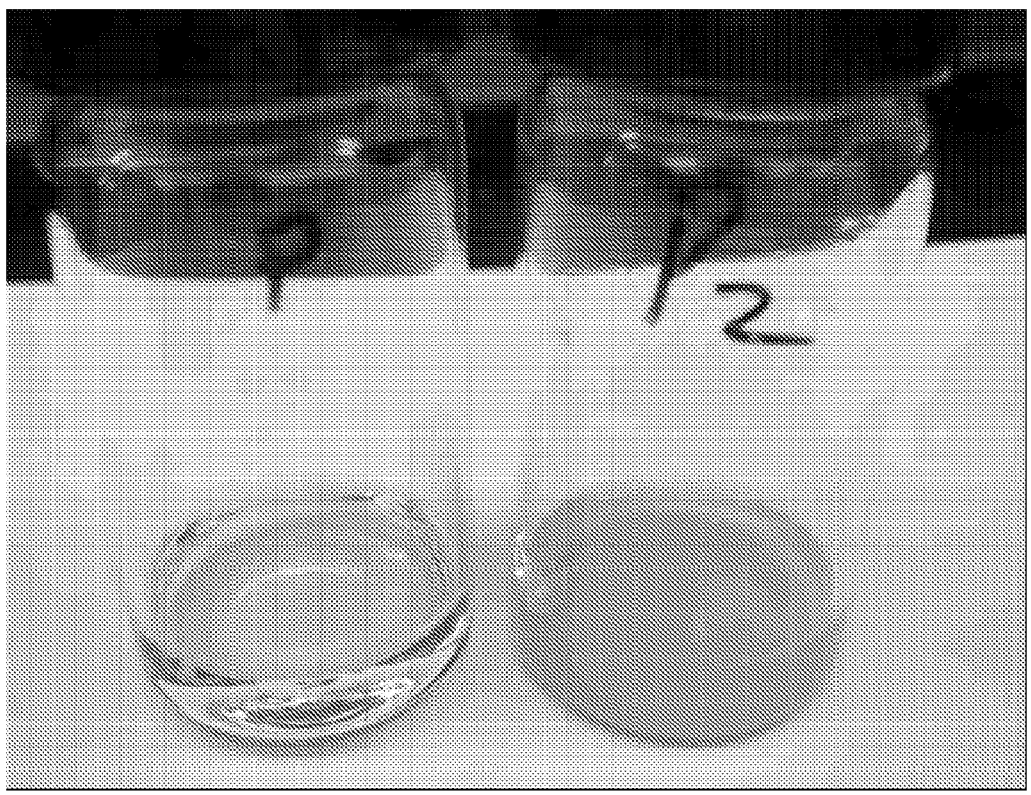
FIG. 23 represents a photographic image illustrating the low temperature stability of PluroGel comprising silver nanoparticles after 4 days at 4° C. (23A—PluroGel; 23B—PluroGel comprising silver nanoparticles).

Characterizations:

Silver nanoparticles exhibited a golden yellow to blue color due to its unique surface plasmon resonance (see FIGS. 22-25). FIG. 22 photographically illustrates silver particles formed using Procedure 1 as described above. Three vials, labeled A, B, and C are depicted. The photograph of FIG. 22 also demonstrates visually the difference between PluroGel (FIG. 22A), PluroGel plus silver particles at 4° C. (22B), and PluroGel plus silver particles at 37° C. (22C). The phase transition is also apparent (note that the vial labeled C is upside down and the composition had gelled). FIG. 23 illustrates the solutions of FIG. 22 (A and B) after 4 days at 4° C.

Figure 24:
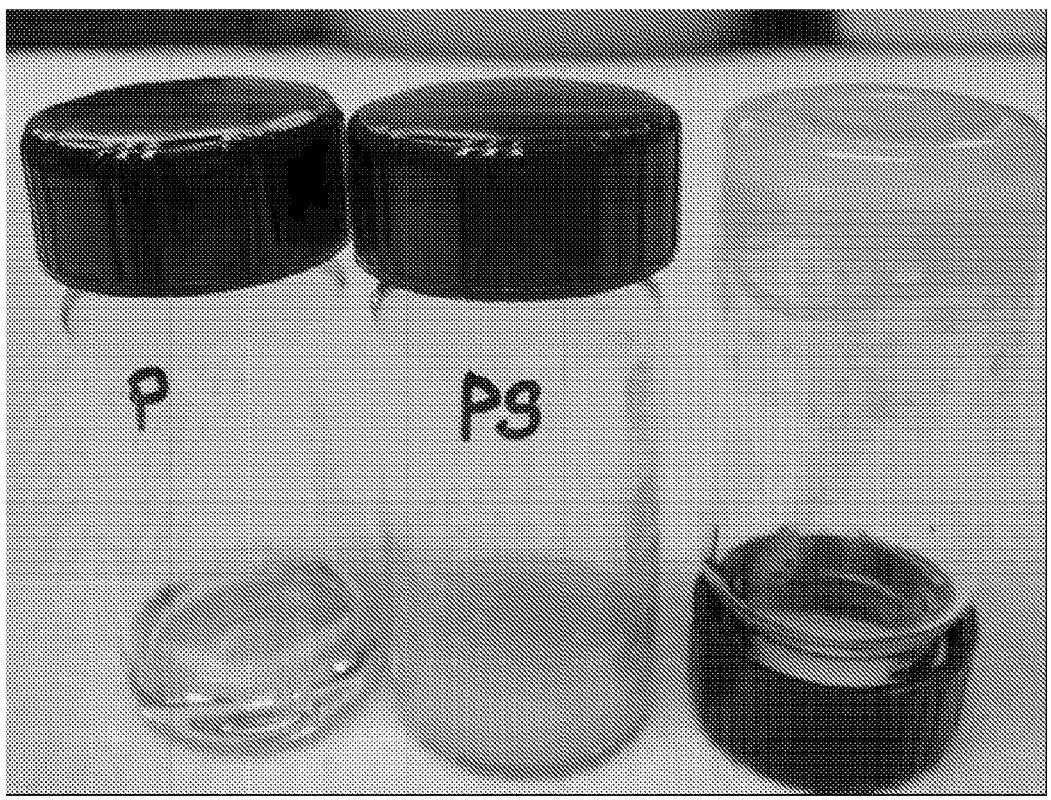
FIG. 24 represents photographic images illustrating the phase transition of PluroGel in the presence of silver particles formed using Procedure 2, as described in Example 2: PluroGel (FIG. 24A); PluroGel plus silver particles at 4° C. (24B); and PluroGel plus silver particles at 37° C. (24C).
Figure 25:
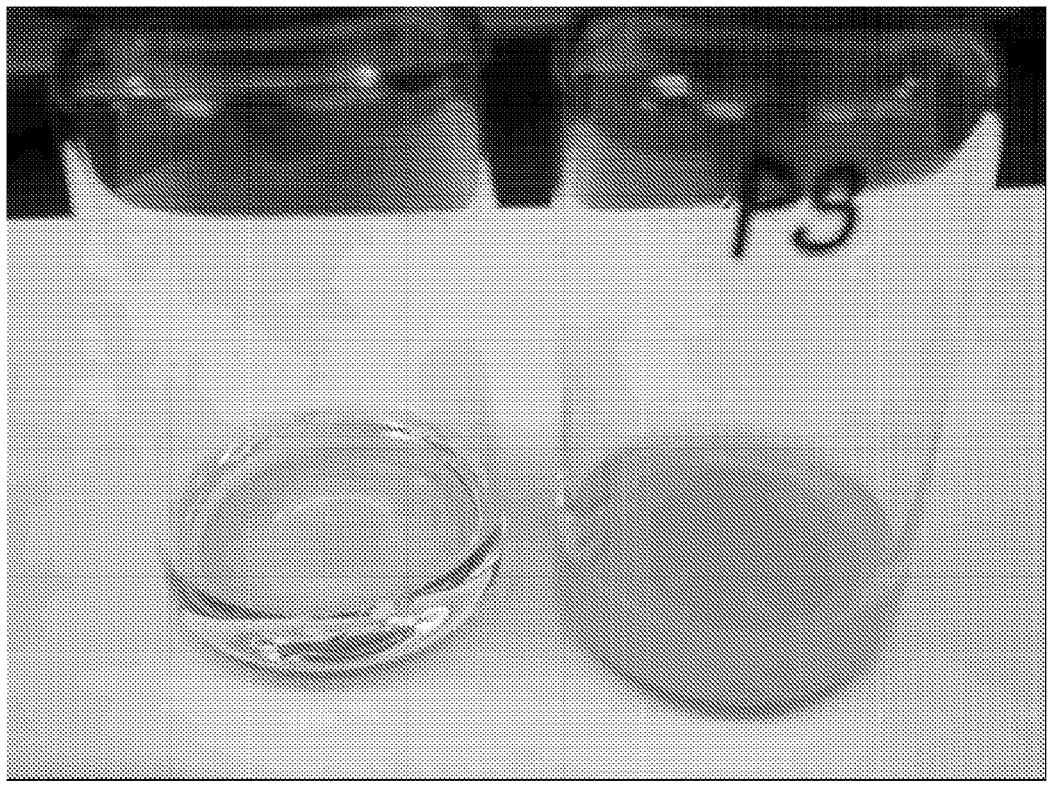
FIG. 25 represents photographic images of the solutions of FIG. 24 (A and B) after 4 days at 4° C.

FIG. 24 photographically illustrates silver particles formed using Procedure 2 described above. The photograph of FIG. 24 also demonstrates visually the difference between Pluro-Gel (FIG. 24A), PluroGel plus silver particles at 4° C. (24B), and PluroGel plus silver particles at 37° C. (24C). The phase transition is also apparent. FIG. 25 illustrates the solutions of FIG. 24 (A and B) after 4 days at 4° C.

Figure 26A:
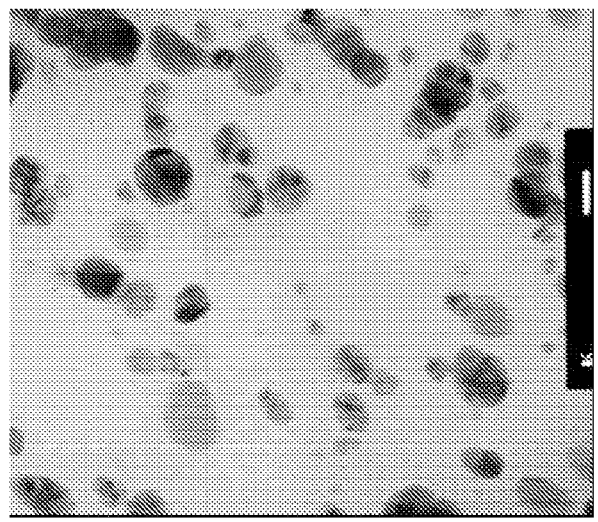
FIGS. 26A-C, represents transmission electron micrographic images providing evidence of the silver nanoparticles prepared according to Procedure 1 of Example 2. It can be seen in FIG. 26A that there are silver nanoparticles and that the general size ranges are about 10-15 nm
Figure 26B:
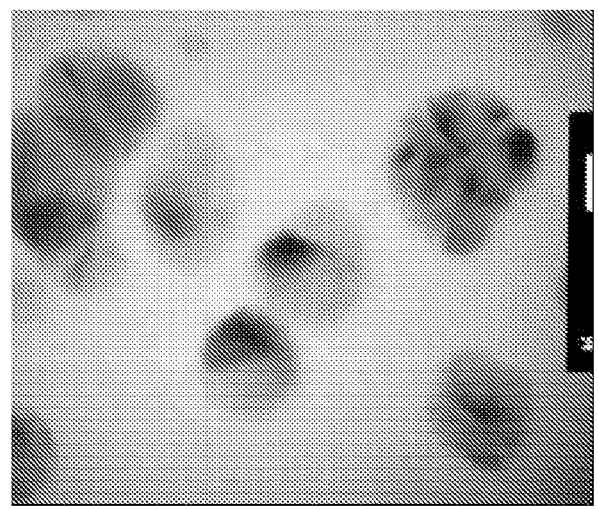
Figure 26C:
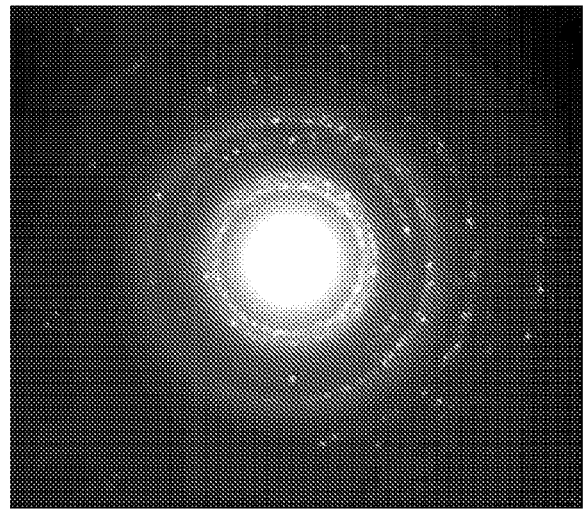

FIG. 26 provides transmission electron micrographic evidence of the silver nanoparticles prepared according to Procedure 1. It can be seen in FIG. 26A that there are silver nanoparticles and that the general size ranges are about 10-15 nm. FIG. 26B represents a higher magnification image of silver nanoparticles and demonstrates the partially crystalline structure. FIG. 26C represents an x-ray diffraction pattern which confirms the partially crystalline structure of the particles. The PluroGel™ composition comprising metallic nanoparticles maintains the physical characteristics of Pluro-Gel without the metallic nanoparticles, e.g., the liquid or gel states temperature dependent.

UV Absorption Spectra:

Even though TEM demonstrated the formation of silver nanoparticles with average size less than 20 nm, the UV visible spectrum of the composite system showed unique peaks. It showed a broad absorption peak covering 275-310 nm presumably due to multivalent silver ions ($Ag_4^{2+}$ and $Ag_2^+$ species), broad peak between 300-350 nm well below the plasmon resonance of silver nanoparticles and has been attributed to atomic clusters of silver and a broad beak with maxima around 430-450 nm indicating the presence of silver nanoparticles. Current research is focused to evaluate the antibacterial efficacy of the composite system as well as to develop methods to control the size of the silver species formed within PluroGel.

Example 3

Tri-Layer Membranes for In Situ Formation of Silver Nanoparticles

Composite films created with nanoparticles evenly dispersed throughout the polymer can have very interesting properties. Layer by layer casting of polyelectrolytes (Chitosan and carboxymethyl chitosan (CMC)) were used to create thin films to form silver nanoparticles in situ.

Methods:

2% solution of chitosan in 0.5% acetic acid and 2% solution of carboxymethyl chitosan in distilled water were used to prepare the layer by layer casted films. Briefly, 6 mL of chitosan was poured into 100 mL petri dish and allowed to dry at 80° C. for 1.5 h. Then 6 mL of carboxymethyl chitosan solution was added and allowed to dry at 80° C. for 1.5 h. After than 6 mL of chitosan was added on top of it and allowed to dry at 80° C. for 1.5 h.

Crosslinking the Films:

Some of the films were further heated to 110° C. for 1 h to crosslink the different polymer layers. All the films were then subjected to neutralization using 0.4N sodium hydroxide solution.

Figure 27A:
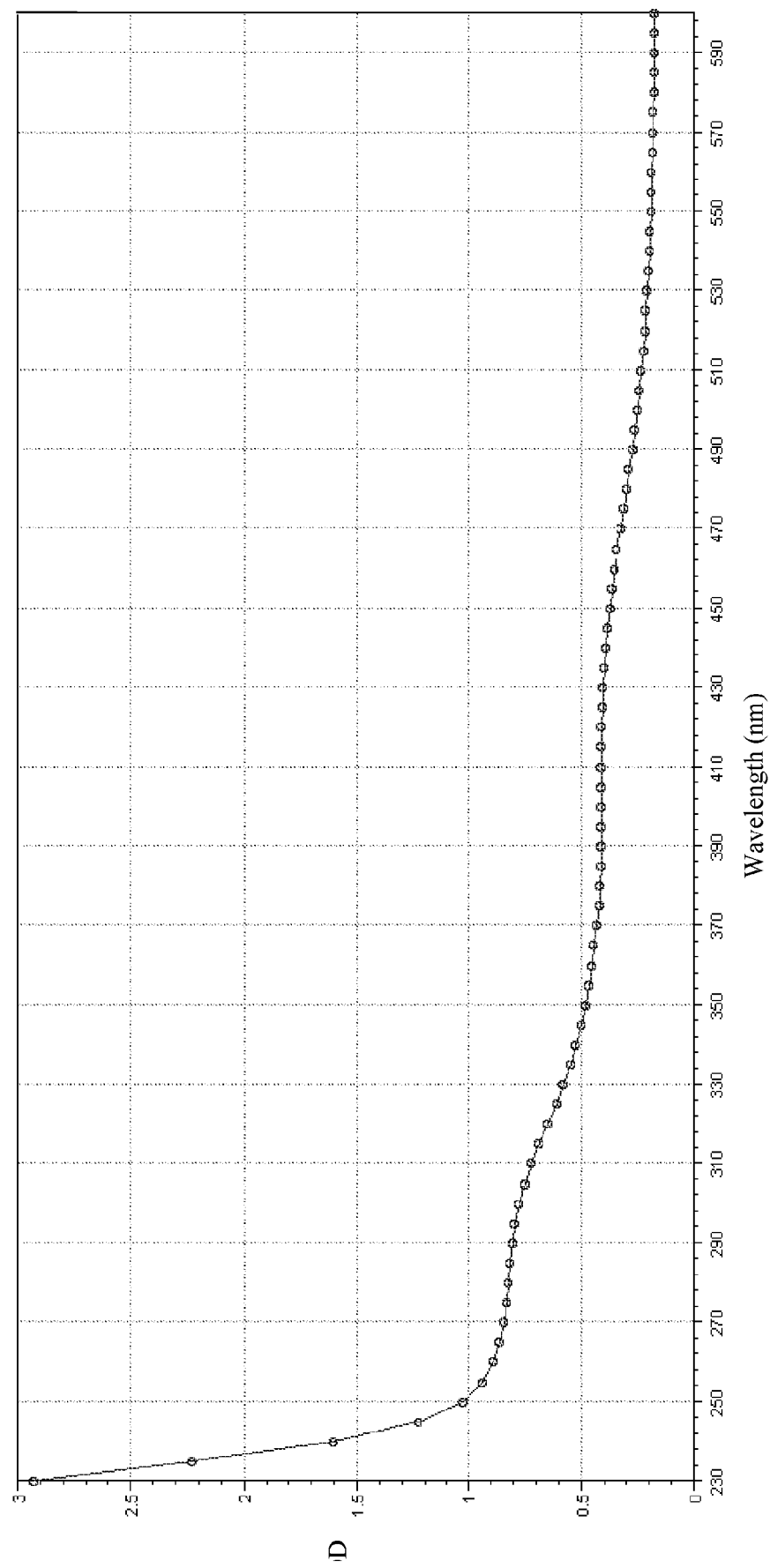
Figure 27B:
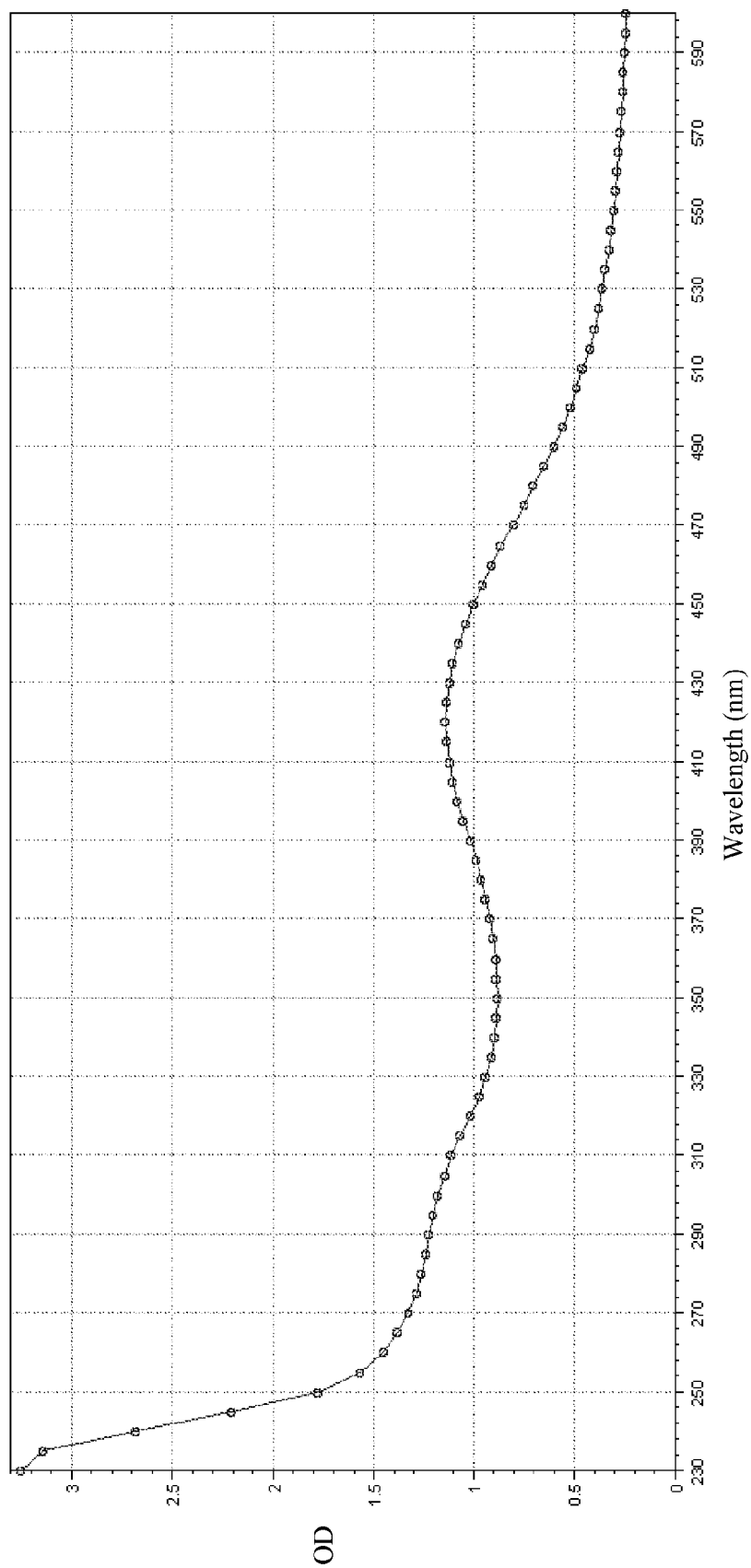
Figure 27C:
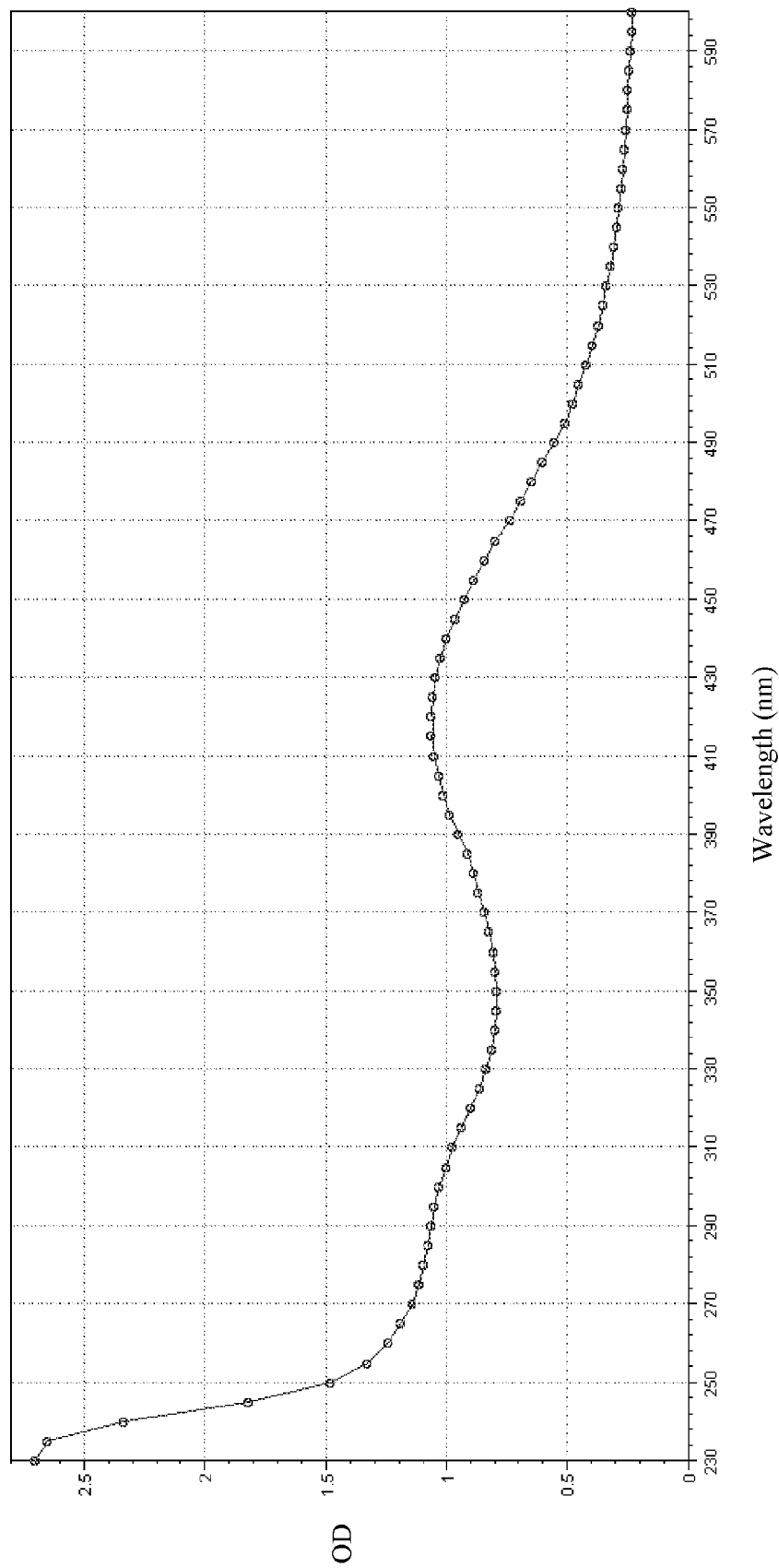
Figure 27D:
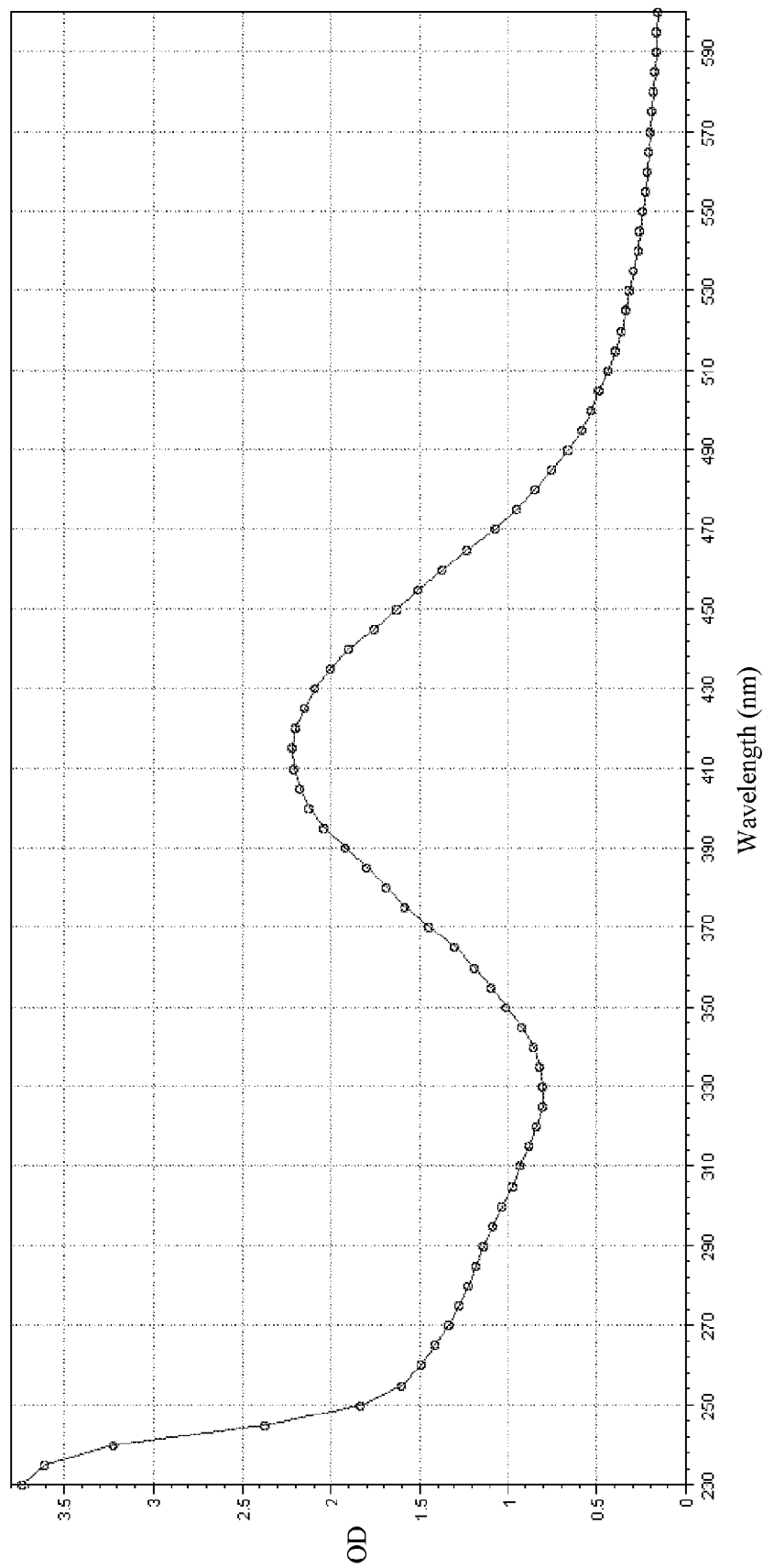

Preparation of Silver Nanoparticles:

We have demonstrated the feasibility of forming silver nanoparticles in the presence of CMC and sodium hydroxide. However, the stability of the particles were found to be very low leading to particle aggregation. There fore trilayer polymer films were used to develop silver particles in situ. After sodium hydroxide treatment, the films were immersed in silver nitrate solution for various periods of time. We have found that after 24 hours the films show characteristic Plasmon resonance of silver nanoparticles indicating the formation of silver particles in situ. FIGS. 27A (1 hour), 27B (3 hours), 27C (5 hours), and 27D (24 hours) provide UV absorption spectra for these experiments. It can be seen that by 3 hours (FIG. 27B), a characteristic peak of silver nanoparticles is present at 410-450 nm, and that by 24 hours (FIG. 27D) there is a significant increase in the peak.

Figure 28:
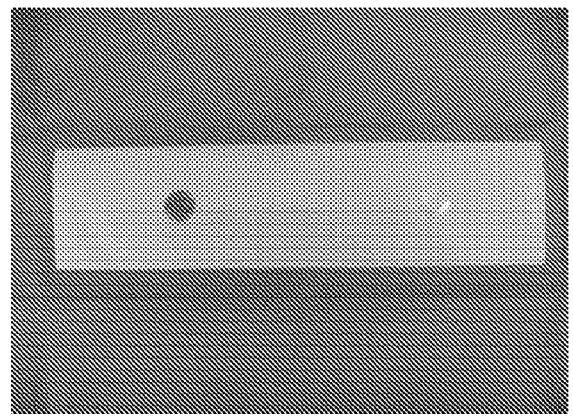
FIG. 28 photographically illustrates a side by side comparison of a trilayer film with silver particles (left film; appears brown in a color photograph) and the control film on the right (no color change).

FIG. 28 photographically illustrates a side by side comparison of a film with silver particles (left film; appears brown in a color photograph) and the control film on the right (no color change).

Figure 29:
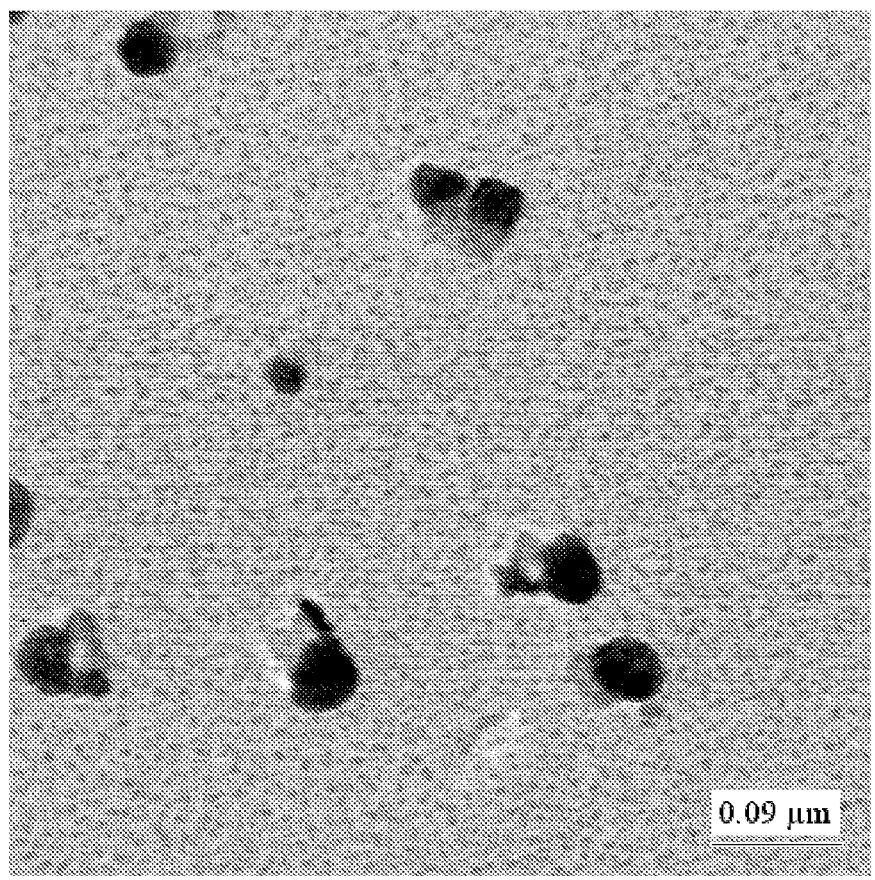
FIG. 29 represents a transmission electron micrograph demonstrating the formation of particles in the middle layer of a trilayer film. The films were sectioned using a cryomicrotome and the cross-section of the film was observed using a transmission electron microscope. A reference length marker indicating 0.09 μm is provided in the lower right portion of the image.

The formation of particles was further confirmed by transmission electron microscopy. The films were sectioned using a cryomicrotome and the cross-section of the film was observed using a transmission electron microscope (see FIG. 29). The study demonstrated the formation of large number of particles in the middle layer, however the chitosan layer also found to have particles and the particles in the chitosan layer was found to be less aggregated compared to the middle layer. Further studies are currently underway to optimize the size and distribution of the particles.

Figure 30:
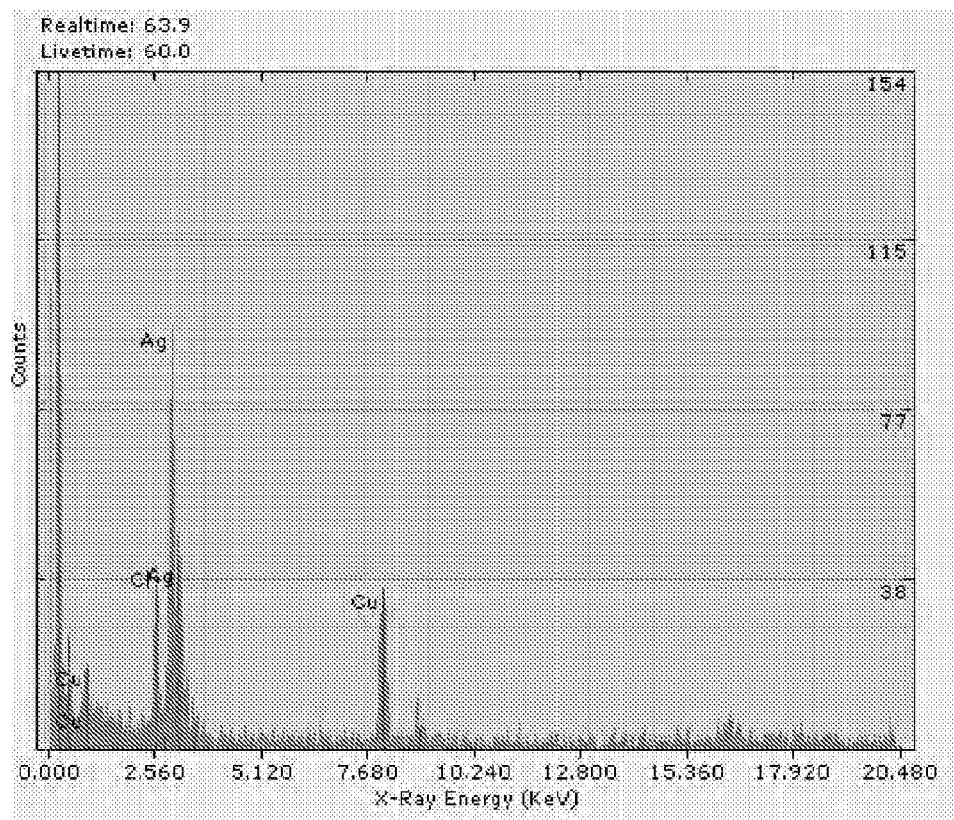
FIG. 30 graphically represents an EDS spectrum of the particles within a trilayer film. The presence of the silver peaks (Ag) confirms the composition of the particles. The ordinate represents counts. The abscissa represents x-ray energy in KeV.

A trilayer film was also subjected to energy-dispersive x-ray microanalysis. The results (FIG. 30) indicate the elemental contents of the particles in the film. FIG. 30 graphically represents an EDS spectrum of the particles within the trilayer film. The presence of the silver peaks (Ag) confirms the composition of the particles.

Figure 31:
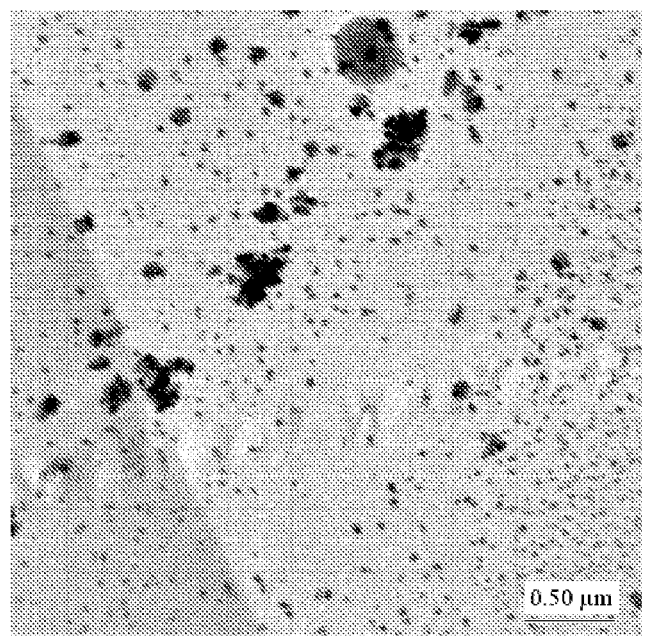
FIG. 31 represents an image of a transmission electron micrograph illustrating the distribution of silver particles within a trilayer film. More particle aggregates are found along the CMC layer compared to the chitosan layer. A reference length marker indicating 0.50 μm is provided in the lower right portion of the image.

FIG. 31 represents a photomicrographic image illustrating the distribution of the particles within a trilayer film. More particle aggregates are found along the CMC later compared to the chitosan layer. The marker in the photograph represents 50 µm.

Other methods for forming and using compositions comprising chitosan are known in the art and such methods and compositions are encompassed by the present application. Such methods and compositions are described in, for example, International Patent Publication WO 2007/087350 (Laurencin et al.) published Aug. 2, 2007, the contents of which are hereby incorporated by reference in their entirety.

Example 4

Uses of Titanium Films

Materials and Methods:

Titanium metal foil (0.25 mm) was procured from Good Fellow, Cambridge Ltd. Sodium hydroxide, silver nitrate, sodium borohydride and ethanol were procured from Sigma Aldrich (St, Louis USA). Human bone marrow-derived mesenchymal stem cells (hMSCs) were obtained from Cambrex and E. coli from ATCC.

Titanium samples (1×1 cm) were then incubated in 5 M sodium hydroxide solution at 40° C. for 24 h. hMSCs were cultured for 14 days on modified titanium surfaces using basal growth media. Cell proliferation was determined using MTS colorimetric assay and alkaline phosphatase activity using standard alkaline phosphatase kit.

The base etched films were incubated in 50 mM aqueous silver nitrate solution at 40° C. for 24 h. The films were then washed with a mild reducing agent such as 70% ethanol and then exposed to 10 mM aqueous sodium borohydride solution for 2-3 minutes. A fast reaction occurred and the color of the metal foil changed to dark brown. The modified substrates were further washed with 70% ethanol, twice with distilled water and dried under vacuum.

Results

The morphology of the metal surfaces, both before and after surface modifications, was evaluated using secondary electron imaging (SEI) in a JEOL 6700F scanning electron microscope (SEM). The elemental composition of the modified surface was evaluated using energy dispersive spectroscopy (PGT Light Element Detector running Spirit software).

Figure 32A:
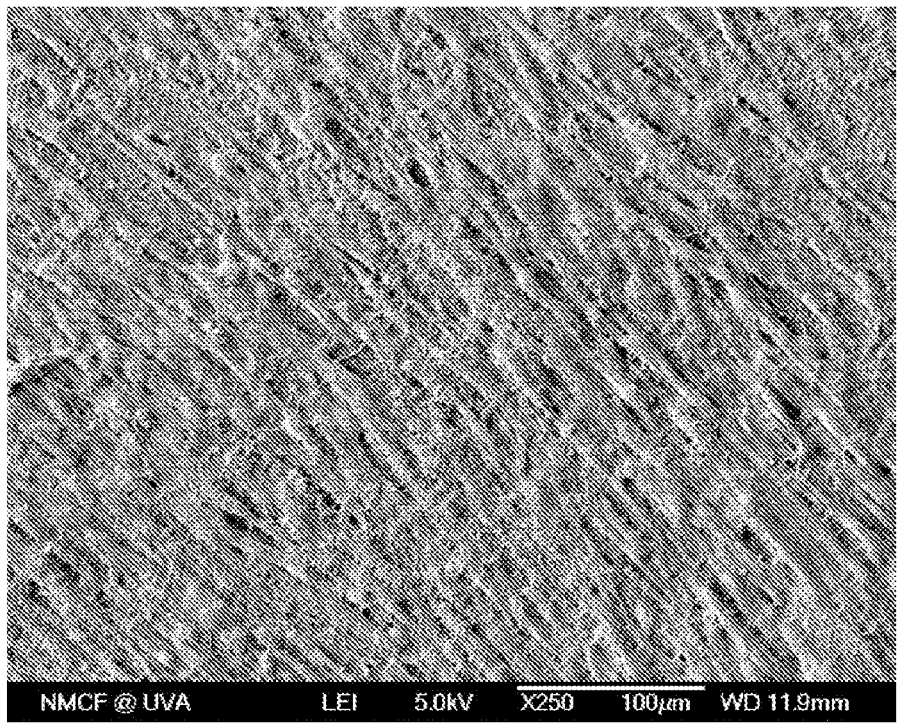
FIGS. 32A and 32B, represents the surface morphology of titanium thin films illustrated by scanning electron microscopic images.
Figure 32B:
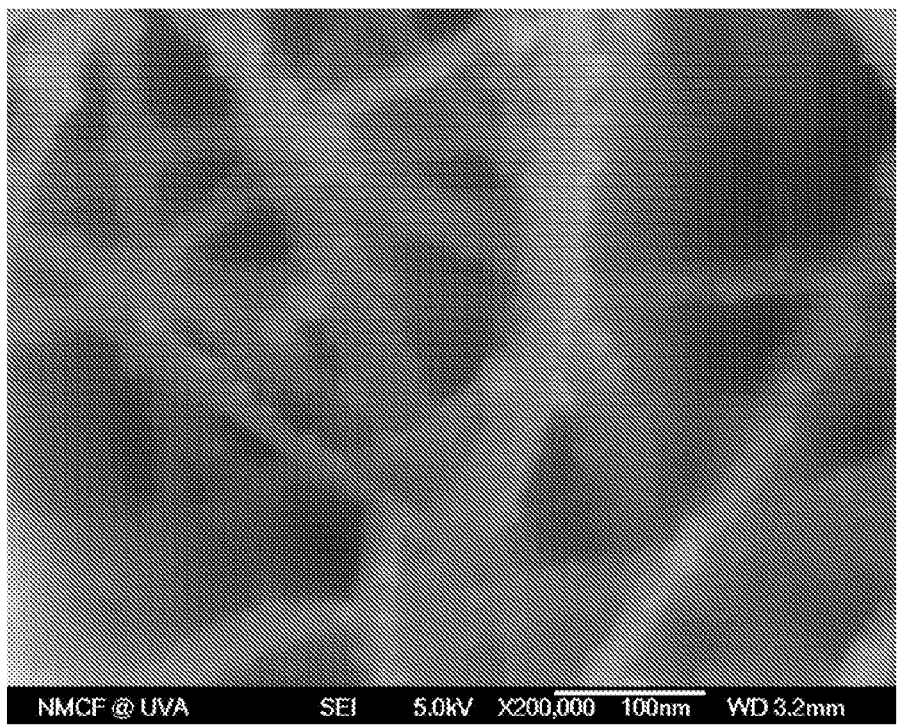

The base etched titanium films were found to be cytocompatible as evidenced by the proliferation of human mesenchymal stem cells on the surface (FIG. 32A). The cells on nanostructured film showed higher alkaline phosphatase activity compared to control film. FIG. 32B shows the presence of near spherical shaped silver nanoparticles on the nanofibrous structures with a mean diameter of ~10 nm. This is highly significant since previous studies have demonstrated that the shape and size of the silver nanoparticles plays a significant role in its antibacterial activity with highest activity found for particles with sizes ranging from 1-10 nm. The composition of the silver nanoparticles was further confirmed by EDS. The high antibacterial property of surfaces containing silver nanoparticles was demonstrated using E. coli.

Conclusions

The development of nanostructured implants can be considered as one of the promising strategies to increase osseointegration and provides matrices to be used to deliver cells such as hMSCs to an osseous defect and reduce implant associated infection. The study shows a versatile technique to develop nanostructured titanium containing silver nanoparticles as a potential biomaterial.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Accordingly, the present invention is not intended to be limited to the embodiments shown herein but is to be accorded the widest scope consistent with the principles and novel features disclosed herein.

BIBLIOGRAPHY

1. R. J. Gehr, R. W. Boyd, Chem. Mater. 8 (1996) 1807.
2. R. Patakfalvi, Z. Viranyi, I. Dekany. Colloid Polym Sci. 283 (2004) 299.
3. Shon Y S, Colorado R, Williams C T, Bain C D, Lee T R. Langmuir, 2000, 16: 541.
4. Limsavarn L, Sritaveesinsub V, Dubas S T. Materials Letters 61: 2007, 3048-51.
5. Zhao S, Zhang K. An J, Sun Y, Sun C. Mater Lett 60; 2006; 1215.
6. Dokoutchaev A, James J T, Koene S C, Pathak S, Surya prakash GK, Thompson M E. Chem Mater 1999; 11: 2389.
7. Kobayashi Y, Salguerino-Maceira V, Liz-Marzan Chem Mater 2001; 13: 1630.
8. Wang D, Salgueirino-Maceira, Liz-Marzan L M, Caruso F. Adv Mater 2002; 14: 908
9. Pol V G, Grisaru H, Gedanken A. Langmuir, 2005; 21: 3635
10. Sant S B, K. S. Gill b, R. E. Burrell c g Acta Biomaterialia 2007; 3: 341
11. Wright J B, Lam K, Buret A G, Olson M E, Burrell R E. Wound Repair Regeneration. 2002; 10: 141.
12. Masuka K, Ishihara M, Asazuma T, Hattori H et alBiomaterials 26 (2005) 3277-3284

13. Yin Y, Li Z, Zhong Z, Gates B, Xia Y, Venkataeswaran S. J Mater Chem 2002; 12: 522-527.

What is claimed is:

1. A thermo-gelling solution comprising chitosan and ammonium hydrogen phosphate, wherein the ratio of chitosan to ammonium hydrogen phosphate is between about 1.0 and about 3.5, wherein said thermo-gelling solution is a solution at a pH between about 6.0 and about 8.0 and at a temperature below about 20° C., further wherein said solution forms a gel within a temperature range from about 20° C. to about 50° C., further wherein said solution comprises metallic nanoparticles.

2. The thermo-gelling solution of claim 1, wherein said metallic nanoparticles are silver nanoparticles.

3. The thermo-gelling solution of claim 1, wherein the concentration of chitosan ranges from about 0.05% to about 10.0% and the concentration of ammonium hydrogen phosphate ranges from about 0.5% to about 2.8%.

4. The thermo-gelling solution of claim 1, comprising about 2% chitosan.

5. The thermogelling solution of claim 1, wherein said chitosan is carboxymethyl chitosan.

6. The thermogelling solution of claim 1, wherein the nanoparticles range in size from about 1.0 nm to about 100 nm.

7. The thermogelling solution of claim 6, wherein the nanoparticles range in size from about 2.0 nm to about 75 nm.

8. The thermogelling solution of claim 7, wherein the nanoparticles range in size from about 3.0 nm to about 50 nm.

9. The thermogelling solution of claim 1, wherein the nanoparticles range in size from about 5.0 nm to about 10.0 nm.

10. The thermogelling solution of claim 1, wherein said metallic nanoparticle is useful as an antimicrobial.

11. The thermogelling solution of claim 1, wherein said chitosan has a molecular weight of between about 20,000 and 250,000.

* * * * *